US008247507B2

(12) United States Patent
Garcia Castro et al.

(10) Patent No.: US 8,247,507 B2
(45) Date of Patent: Aug. 21, 2012

(54) CATIONIC POLYMERS AS THICKENERS FOR AQUEOUS AND ALCOHOLIC COMPOSITIONS

(75) Inventors: Ivette Garcia Castro, Ludwigshafen (DE); Son Nguyen Kim, Hemsbach (DE); Wolfgang Jahnel, Bellheim (DE); Matthias Laubender, Schifferstadt (DE); Rolf Werner, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 257 days.

(21) Appl. No.: 12/442,227

(22) PCT Filed: Sep. 14, 2007

(86) PCT No.: PCT/EP2007/059692
§ 371 (c)(1),
(2), (4) Date: Mar. 20, 2009

(87) PCT Pub. No.: WO2008/034767
PCT Pub. Date: Mar. 27, 2008

(65) Prior Publication Data
US 2010/0040573 A1 Feb. 18, 2010

(30) Foreign Application Priority Data

Sep. 21, 2006 (EP) .................................... 06121075

(51) Int. Cl.
*C08F 26/00* (2006.01)
*C08F 2/00* (2006.01)
(52) U.S. Cl. ....... 526/263; 526/89; 526/303.1; 526/310; 526/209
(58) Field of Classification Search .................. 526/109, 526/209, 89, 303.1, 310, 263
See application file for complete search history.

(56) References Cited

U.S. PATENT DOCUMENTS

| 3,405,084 | A | | 10/1968 | Bohac et al. |
| 4,058,491 | A | | 11/1977 | Steckler |
| 4,845,147 | A | * | 7/1989 | Blum et al. .................. 524/461 |
| 4,917,886 | A | | 4/1990 | Asche et al. |
| 5,093,412 | A | | 3/1992 | Mente et al. |
| 6,277,386 | B1 | | 8/2001 | Kim et al. |
| 6,482,917 | B1 | | 11/2002 | Hildebrandt et al. |
| 6,682,725 | B1 | | 1/2004 | Dieing et al. |
| 2009/0010865 | A1 | | 1/2009 | Kim et al. |
| 2009/0257960 | A1 | | 10/2009 | Kim et al. |
| 2010/0068156 | A1 | | 3/2010 | Kim et al. |
| 2010/0174040 | A1 | | 7/2010 | Kim et al. |

FOREIGN PATENT DOCUMENTS

| DE | 1694366 | 11/1970 |
| DE | 2150557 | 6/1972 |
| DE | 2541865 | 4/1976 |
| DE | 2817369 | 10/1978 |
| DE | 3336047 | 4/1984 |
| DE | 3708451 | 10/1988 |
| DE | 3929973 | 3/1991 |
| DE | 4223066 | 1/1994 |
| DE | 4225045 | 2/1994 |
| DE | 4333238 | 4/1995 |
| DE | 19731907 | 1/1999 |
| DE | 19807908 | 8/1999 |
| DE | 19833287 | 1/2000 |
| DE | 10354015 | 6/2005 |
| EP | 257444 | 3/1988 |
| EP | 275563 | 7/1988 |
| EP | 450123 | 10/1991 |
| EP | 480280 | 4/1992 |
| EP | 636361 | 2/1995 |
| EP | 670342 | 9/1995 |
| EP | 687694 | 12/1995 |
| EP | 0751162 | 1/1997 |
| EP | 0893117 | 1/1999 |
| EP | 1064924 | 1/2001 |
| EP | 1084696 | 3/2001 |
| WO | WO-9322380 | 11/1993 |
| WO | WO-9325595 | 12/1993 |
| WO | WO-9725021 | 7/1997 |
| WO | WO-9904750 | 2/1999 |
| WO | WO-0113884 | 3/2001 |
| WO | WO-03080001 | 10/2003 |
| WO | WO-03099253 | 12/2003 |
| WO | WO-2004035635 | 4/2004 |
| WO | WO-2004100910 | 11/2004 |
| WO | WO-2005003200 | 1/2005 |

OTHER PUBLICATIONS

Cumene hydroperoxide, Wikipedia.com, 1 page (Mar. 28, 2011).*
Tert-butyl peroxybenzoate, Chemicalland21.com, 1 page (Mar. 28, 2011).*
Bruce Martin's O-Protonation of Amides in Dilute Acids, J.C.S. Chem. Comm., 1972, 793-794.*
Mark et al., "Peroxy Compounds", Encyclopedia of Polymer Science and Engineering Edition 2, vol. 11, 1988, pp. 1-21.
Gezondheidsraad Health Council of the Netherlands, "Azobisisobutyronitrile. Health-based recommended occupational exposure limit", Mar. 12, 2002.
International Preliminary Report on Patentability (IPRP) for International application PCT/EP2007/059692, mailed Apr. 16, 2009.
U.S. Appl. No. 12/674,581, filed Feb. 22, 2010, Kim et al.
U.S. Appl. No. 12/865,755, filed Aug. 2, 2010, Kim et al.
U.S. Appl. No. 13/062,197, filed Mar. 3, 2011, Kim et al.

* cited by examiner

*Primary Examiner* — David W Wu
*Assistant Examiner* — Vu A Nguyen
(74) *Attorney, Agent, or Firm* — Connolly Bove Lodge & Hutz LLP

(57) ABSTRACT

The present invention relates to a method for producing polymers by radically polymerizing a mixture comprising 99.99 to 10% by weight of at least one α,β-ethylenically unsaturated compound with at least one cationogenic and/or cationic group per molecule, 0 to less than 25% by weight of at least one monoethylenically unsaturated amide-group-containing compound different from a) and also 0.01 to 5% by weight of a crosslinker using at least two different water-insoluble initiators.

17 Claims, No Drawings

CATIONIC POLYMERS AS THICKENERS FOR AQUEOUS AND ALCOHOLIC COMPOSITIONS

CROSS REFERENCE TO RELATED APPLICATIONS

This application is a National Stage of PCT/EP2007/059692 filed Sep. 14, 2007 which in turn claims priority from European Application 06121075.3 filed Sep. 21, 2006, the entire contents of which are incorporated herein by reference.

The present invention relates to a method for producing polymers by radically polymerizing a mixture comprising 99.99 to 10% by weight of at least one $\alpha,\beta$-ethylenically unsaturated compound with at least one cationogenic and/or cationic group per molecule, 0 to less than 25% by weight of at least one monoethylenically unsaturated amide-group-containing compound different from a) and also 0.01 to 5% by weight of a crosslinker using at least two different water-insoluble initiators.

Polymers are used widely in hair cosmetics. Their task in hair cosmetics is to influence the properties of the hair, in particular to give the hair hold, to improve combability and to impart a pleasant feel to the touch.

Thus, conditioners are used for improving the dry and wet combability, feel, shine and appearance, and also for imparting antistatic properties to the hair. Preference is given to using water-soluble polymers with polar, often cationic functionalities which have a relatively great affinity to the surface of the hair, which is negative due to its structure. The structure and mode of action of various hair treatment polymers are described in Cosmetic & Toiletries 103 (1988) 23. Standard commercial conditioner polymers are, for example, cationic hydroxyethylcellulose, cationic polymers based on N-vinylpyrrolidone, e.g. copolymers of N-vinylpyrrolidone and quarternized N-vinylimidazole, acrylamide and diallyidim-ethylammonium chloride or silicones.

For setting hairstyles, vinyllactam homopolymers and copolymers and carboxylate-group-containing polymers are used. Requirements of hair setting resins are, for example, strong hold at high atmospheric humidity, elasticity, ability to be washed out of the hair, compatibility in the formulation and a pleasant feel of the hair.

The combination of different properties such as, for example, pleasant feel of the hair, setting and simultaneous thickening effect of the polymers in the hair cosmetic preparations often presents difficulties.

This is of importance especially in gel formulations. Moreover, customary setting polymers often exhibit incompatibilities with thickening polymers, resulting in turbidity and precipitations in the cosmetic formulations. Classic thickeners, which consist either of crosslinked polyacrylic acid (carbopol) or copolymers, have the disadvantage that, on account of the crosslinking, they do not form films which are suitable for setting hair. They ensure the consistency of the gel, but after the gel has dried on the hair, they are no longer required and therefore potentially disrupt the application-related and esthetic properties of the formulation (setting effect, moisture sensitivity, clarity, gel structure). In addition, rheology-modifying agents are also used in pharmaceutical preparations. Thus, preparations for topical application, such as ointments, creams, gels, emulsions or drops, in particular comprise the viscosity-influencing agents. Corresponding agents are also to be found in syrups.

Agents often used in pharmaceutical preparations for this purpose are the already mentioned carbopols (CTFA name "Carbomer"). For the application, these have to be neutralized with inorganic or organic bases, as a result of which the pH increases. The thickening effect is thus pH-dependent. In acidic conditions, the thickening effect is inadequate.

Moreover, the required neutralization of the carbomers presents problems when using active ingredient acids, especially for topical applications. The active ingredients then have to be converted into their salts in the preparation, which, in the case of uptake via the skin, hinders absorption.

Added to this is the fact that active ingredients which are unstable in alkaline conditions, such as, for example, ascorbic acid, have a tendency to decompose in the presence of neutralized carbomers.

PRIOR ART

WO 04/100910 (BASF) describes cosmetic compositions which comprise at least one polymer obtainable by radically polymerizing $\alpha,\beta$-ethylenically unsaturated compounds which each comprise at least one nitrogen-containing heterocycle, in the presence of a polymeric graft base. In particular, vinylpyrrolidone-vinylimidazole copolymers prepared in the presence of polyethylene glycol are described. The described polymers are not crosslinked.

WO 93/22380 (ISP) discloses hydrogels, adhesive and coatings comprising crosslinked copolymers of 80-99% by weight of N-vinylpyrrolidone and 1 to 20% by weight of N-vinylimidazole or 4-vinylpyridine which have been prepared by solution polymerization in water. The use of at least 2 different initiators during the production of the cationic polymers is not described.

DE 198 33 287 (BASF) describes the production of polymers from (a1) 5 to 99.99% by weight of a radically polymerizable monomer which comprises a quaternized or quaternizable nitrogen atom, or mixtures of such monomers, (a2) 5 to 95% by weight of an N-vinyllactam, (b) 0.01 to 20% by weight of a crosslinking monomer with at least two ethylenically unsaturated groups, and (c) 0 to 50% by weight of a further radically polymerizable monomer in supercritical carbon dioxide as inert diluent with mixing at temperatures of above 31° C. to 150° C. and pressures above 73 bar. The use of at least 2 different water-insoluble initiators during the production of the cationic polymers is not described.

DE 197 31 907 (BASF) describes crosslinked cationic polymers of vinylimidazole and N-vinylpyrrolidone which are produced by gel polymerization, inverse suspension polymerization or inverse emulsion polymerization in aqueous solvent mixtures. The use of at least 2 different water-insoluble initiators during the production of the cationic polymers is not described.

WO 93/25595 describes crosslinked cationic copolymers based on quaternized dialkylaminoalkyl acrylates or dialkylaminoalkylacrylamides. The use of at least 2 different water-insoluble initiators during the production of the cationic polymers is not described.

EP-A 687694 describes a method for producing polymers based on vinylimidazoles by radical precipitation polymerization in an organic solvent or solvent mixture which comprises no aromatic groups and, apart from oxygen, no heteroatom. The use of at least 2 different water-insoluble initiators is not described.

EP A 0 893 117 and EP 1 064 924 describe the use of high molecular weight crosslinked cationic polymers as solution polymers. These have a good conditioning effect in shampoos. The use of at least 2 different water-insoluble initiators during the production of the cationic polymers is not described.

DE C 33 36 047 describes topically applicable compositions of the active ingredient diclofenac which comprise carbomer neutralized with secondary organic amines as thickener.

EP-A 450 123 describes diclofenac-sodium-comprising compositions for topical application which, to avoid the disadvantages associated with a neutralization using secondary organic amines, comprise cellulose derivatives as thickeners.

OBJECT OF THE INVENTION

An object of the present invention was a method for producing polymers which, as the sole ingredient besides water and/or alcohol of a clear aqueous, alcoholic or aqueous/alcoholic preparation, permit a thickening of the preparation in the lowest possible concentrations.

It was a further object of the present invention to find polymers which are highly suitable for cosmetic applications and, particularly in the field of hair cosmetics, have good application properties such as pleasant feel, good conditioning and setting effect effect and simultaneous thickening properties. In addition, visual clarity of the preparations comprising the polymers, in particular of the gels, and also a good gel structure are also of importance.

The polymers to be provided should also ensure high stability of the resulting compositions toward salts and also be compatible with the cosmetically customary polymers in the pH range from 5 to 8.

It was also an aim to provide polymers which permit effective rheology modification even over the broadest possible pH range. The polymers should of course be accessible in a cost-effective manner and, following their production, require the fewest possible work-up measures.

A further object of the invention was the provision of polymers as thickeners for pharmaceutical preparations, in particular for preparations for topical application. The object related in particular to the provision of polymers which have a thickening effect over a broad pH range from 1 to 10. In addition, the object was also to find thickening agents for pharmaceutical preparations which develop an adequate effect even in small concentrations. In addition, the polymers to be provided should help to avoid the problem of salt formation in the case of active ingredient acids. It was also an aim of the present invention to find gel formulations for active ingredients which are sensitive in a basic or neutral medium.

1. The aforementioned objects were achieved by polymers obtainable by a method for producing polymers by radically polymerizing
    a) 99.99 to 10% by weight of at least one α,β-ethylenically unsaturated compound with at least one cationogenic and/or cationic group per molecule,
    b) 0 to less than 25% by weight of at least one monoethylenically unsaturated amide-group-containing compound different from a),
    c) 0.01 to 5% by weight of a crosslinker,
    d) 0 to 15% by weight of at least one monoethylenically unsaturated compound d1) comprising at least one group selected from the group consisting of optionally substituted $C_5$-$C_{30}$-alkyl, $C_5$-$C_{30}$-alkenyl, $C_5$-$C_8$-cycloalkyl, aryl, arylalkyl and hetaryl and/or a reactive precursor d2) of component d),
    e) 0 to 30% by weight of further monoethylenically unsaturated compounds different from a) to d),
    with the proviso that the amounts of components a) to e) add up to 100% by weight,
    in the presence of
    f) 0 to 70% by weight, based on the sum of components a) to e), of a polyether-containing compound,
    wherein
    in the course of the process at least two different water-insoluble initiators A and B are used.

A preferred embodiment of the invention is polymers obtainable by the aforementioned method where the α,β-ethylenically unsaturated compound a) is selected from
    ai) esters of α,β-ethylenically unsaturated mono- and dicarboxylic acids with amino alcohols which may be mono- or dialkylated on the amine nitrogen,
    aii) amides of α,β-ethylenically unsaturated mono- and dicarboxylic acids with diamines which have at least one primary or secondary amino group,
    aiii) N,N-diallylamines,
    aiv) vinyl- and allyl-substituted nitrogen heterocycles,
    av) vinyl- and allyl-substituted heteroaromatic compounds and
    avi) mixtures thereof.

Within the context of the present invention, the expression "alkyl" comprises straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethyl butyl, 2-ethyl butyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. Preference is given here to predominantly linear alkyl radicals, as also arise in natural or synthetic fatty acids and fatty alcohols, and also oxo alcohols, which may, if appropriate, additionally be mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

"Cycloalkyl" is preferably $C_5$-$C_8$-cycloalkyl, such as cyclopentyl, cyclohexyl, cycloheptyl or cyclooctyl.

Within the context of the present invention, the expression "heterocycloalkyl" comprises saturated, cycloaliphatic groups having generally 4 to 7, preferably 5 or 6, ring atoms, in which 1 or 2 of the ring carbon atoms are replaced by heteroatoms selected from the elements oxygen, nitrogen and sulfur, and which may be optionally substituted, where in the case of a substitution, these heterocycloaliphatic groups can carry 1, 2 or 3, preferably 1 or 2, particularly preferably 1, substituents, selected from alkyl, aryl, COOR, $COO^-M^+$ and $NE^1E^2$, preferably alkyl. By way of example of such heterocycloaliphatic groups, mention may be made of pyrrolidinyl, piperidinyl, 2,2,6,6-tetramethyl piperidinyl, imidazolidinyl, pyrazolidinyl, oxazolidinyl, morpholidinyl, thiazolidinyl, isothiazolidinyl, isoxazol idinyl, piperazinyl, tetrahydrothiophenyl, tetrahydrofuranyl, tetrahydropyranyl, dioxanyl.

"Aryl" comprises unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

Substituted aryl radicals preferably have 1, 2, 3, 4 or 5, in particular 1, 2 or 3, substituents selected from alkyl, alkoxy, carboxyl, carboxylate, trifluoromethyl, —$SO_3H$, sulfonate, $NE^1E^2$, alkylene-$NE^1E^2$, nitro, cyano or halogen.

"Hetaryl" is preferably pyrrolyl, pyrazolyl, imidazolyl, indolyl, carbazolyl, pyridyl, quinolinyl, acridinyl, pyridazinyl, pyrimidinyl or pyrazinyl.

"Arylalkyl" is groups which comprise both alkyl and aryl radicals, these arylalkyl groups being linked to the compound carrying them either via the aryl radical or via the alkyl radical.

Monomer a)

Monomers a) suitable for the method according to the invention are, for example, generally the compounds referred to in WO 03/080001 on p. 18, I.27 to p. 22, I.38 as "direct precursors a2", to which reference is hereby made in its entirety. "Cationogenic" is understood as meaning the ability of a molecule to be able to be converted to the cationic charge state by protonation/quaternization.

Suitable cationogenic monomers a) are ai) the esters of α,β-ethylenically unsaturated mono- and dicarboxylic acids with amino alcohols. Preferred amino alcohols are $C_2$-$C_{12}$-amino alcohols, which are $C_1$-$C_8$-mono- or -dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof.

Suitable monomers a) are also aii) the amides of the aforementioned α,β-ethylenically unsaturated mono- and dicarboxylic acids with diamines which have at least one primary or secondary amino group. Preference is given to diamines which have one tertiary and one primary or secondary amino group.

Preferred acid components are acrylic acid, methacrylic acid and mixtures thereof.

Preferred esters ai) or amides aii) of α,β-ethylenically unsaturated mono- and dicarboxylic acids with amino alcohols or diamines are thus aminoalkyl(meth)acrylates and aminoalkyl(meth)acrylamides of the general formula I:

$$R^{14} \text{~~} \overset{R^{15}}{\underset{\underset{O}{\parallel}}{C}} - Z - R^{18} - NR^{25}R^{26} \quad [R^{17}]_g \tag{I}$$

where
R$^{14}$ and R$^{15}$ independently of one another are selected from the group consisting of hydrogen, $C_1$-$C_8$ linear or branched-chain alkyl, methoxy, ethoxy, 2-hydroxyethoxy, 2-methoxyethoxy and 2-ethoxyethyl. Preference is given to hydrogen, methyl or ethyl,
R$^{17}$ is hydrogen or methyl,
R$^{18}$ is alkylene or hydroxyalkylene having 1 to 24 carbon atoms, optionally substituted by alkyl, preferably $C_2H_4$, $C_3H_6$, $C_4H_8$, $CH_2$—CH(OH)—$CH_2$,
g is 0 or 1,
Z is nitrogen when g=1 or oxygen when g=0,
R$^{25}$ and R$^{26}$ are each and independently of the other selected from the group consisting of hydrogen, $C_1$-$C_{40}$ linear or branched-chain alkyl, formyl, $C_1$-$C_{10}$ linear or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl. Preference is given to hydrogen, methyl, ethyl, n-propyl and benzyl.

Preferred monomers ai) are, in particular,
N-methylaminoethyl (meth)acrylate, N-ethylaminoethyl (meth)acrylate,
N-(n-propyl)aminoethyl (meth)acrylate, N-(n-butyl)aminoethyl (meth)acrylate,
N-(tert-butyl)aminoethyl (meth)acrylate, N,N-dimethylaminomethyl (meth)acrylate,
N,N-dimethylaminoethyl (meth)acrylate, N,N-diethylaminoethyl (meth)acrylate,
N,N-dimethylaminopropyl (meth)acrylate, N,N-diethylaminopropyl (meth)acrylate and
N,N-dimethylaminocyclohexyl (meth)acrylate. In particular, N-(tert-butyl)aminoethyl acrylate and N-(tert-butyl)aminoethyl methacrylate are used as monomers ai).

The amides can be present in unsubstituted form, N-alkyl or N-alkylamino-monosubstituted or N,N-dialkyl-substituted or N,N-dialkylamino-disubstituted form, in which the alkyl or alkylamino groups are derived from $C_1$-$C_{40}$ linear, $C_3$-$C_{40}$ branched-chain, or $C_3$-$C_{40}$ carbocyclic units.

Preferred monomers aii) are
N-[2-(dimethylamino)ethyl]acrylamide,
N-[2-(dimethylamino)ethyl]methacrylamide, N-[3-(dimethylamino)propyl]acrylamide,
N-[3-(dimethylamino)propyl]methacrylamide, N-[4-(dimethylamino)butyl]acrylamide,
N-[4-(dimethylamino)butyl]methacrylamide, N-[2-(diethylamino)ethyl]acrylamide,
N-[4-(dimethylamino)cyclohexyl]acrylamide, N-[4-(dimethylamino)cyclohexyl]meth-acrylamide, N-[8-(dimethylamino)octyl]methacrylamide, N-[12-(dimethylamino)dodecyl]-methacrylamide, N-[3-(diethylamino)propyl]methacrylamide and
N-[3-(diethylamino)propyl]acrylamide.

In addition, monomer a) can also be selected from aiii) N,N-diallylamines of the general formula II $$\underset{R^{27}}{\overset{}{N}}\diagup\diagdown \tag{II}$$

where R$^{27}$ is hydrogen or $C_1$ to $C_{24}$ alkyl. Particular preference is given to N,N-diallylamine and N,N-diallyl-N-methylamine, in particular N,N-diallyl-N-methylamine. Particular preference is given to N,N-diallyl-N-methylamine, which is commercially available in quaternized form, for example under the name DADMAC (diallyldimethylammonium chloride).

Particularly preferred cationogenic monomers a) are also aiv) vinyl- and allyl-substituted nitrogen heterocycles, such as N-vinylimidazole, N-vinylimidazole derivatives, e.g. N-vinyl-2-methylimidazole, vinyl- and allyl-substituted heteroaromatic compounds, such as 2- and 4-vinylpyridine, 2- and 4-allylpyridine.

Very particular preference is given to N-vinylimidazoles of the general formula (III), in which R$^1$ to R$^3$ is hydrogen, $C_1$-$C_4$-alkyl or phenyl

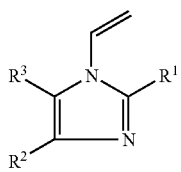
(III)

Examples of compounds of the general formula (III) are given in Table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Most preferred as monomer a) is aiv) N-vinylimidazole, i.e. the compound of the formula III, where all of the radicals $R^1$ to $R^3$ are hydrogen.

The polymer produced by the method according to the invention comprises at most 99.99 and at least 10, preferably at least 30, further preferably at least 60 and particularly preferably at least 70% by weight of copolymerized monomers a).

In particular for the preferred use according to the invention as thickeners in hair cosmetic preparations, polymers with a fraction of at least 60, preferably at least 70% by weight of copolymerized monomers a) are advantageous.

Unless expressly noted otherwise, the data "% by weight" for components a) to e) refer to the sum of 100% by weight of components a) to e).

The conversion of a) to quaternary compounds takes place during or preferably after the reaction. In the case of a subsequent conversion, the intermediate polymer can firstly be isolated and purified or preferably be converted essentially directly. The quaternization can take place completely or partially. In this connection, preferably at least 10%, further preferably at least 20%, particularly preferably at least 30% and in particular at least 50 mol % of the incorporated monomers a) are converted to the corresponding quaternary form. The conversion proportion to quaternary compounds is preferably higher, the lower the solubility in water of a).

It is preferred to use the monomers a) in predominantly, i.e. to more than 70, preferably to more than 90, particularly preferably to more than 95, most preferably to more than 99 mol %, in cationogenic, i.e. nonquaternized or protonated form for the polymerization and to convert them to the quaternized or protonated form by quaternization only during or particularly preferably after the polymerization.

After the polymerization means that 90, preferably 95, further preferably 99 and in particular 99.9% by weight of the monomers a) to e) are copolymerized and are no longer present in polymerizable form.

The quaternization is preferably carried out directly after the polymerization in the polymerization mixture. It is preferred not to undertake further processing steps such as distillation, washing, precipitation or other isolation or purification steps after the polymerization and before the quaternization.

Protonation/Quaternization

In a preferred embodiment of the invention, the polymer is partially or completely protonated or quaternized after the polymerization since the monomer a) used for the polymerization is preferably a non- or only partially quaternized or protonated monomer.

The monomers (a) are preferably polymerized in nonquaternized or nonprotonated form, where, in the latter case, the resulting polymer is preferably quaternized/protonated after the polymerization.

If the monomers are used in quaternized form, they can either be used as dried substance or in the form of concentrated solutions in solvents suitable for the monomers, for example in polar solvents such as water, methanol, ethanol, acetone, in the further components a) to f), if these are suitable as solvents, or in electrolyte solutions.

Of suitability for the protonation are, for example, mineral acids, such as HCl, $H_2SO_4$, and also monocarboxylic acids, e.g. formic acid and acetic acid, dicarboxylic acids and polyfunctional carboxylic acids, e.g. oxalic acid and citric acid, as well as all other proton-releasing compounds and substances which are able to protonate the corresponding nitrogen atom. Of particular suitability for the protonation are water-soluble acids.

Preferred inorganic acids which may be mentioned are phosphoric acid, phosphorous acid, sulfuric acid, sulfurous acid and hydrochloric acid, with phosphoric acid being particularly preferred.

Possible organic acids which may be are mono- and polybasic, optionally substituted aliphatic and aromatic carboxylic acids, mono- and polybasic, optionally substituted aliphatic and aromatic sulfonic acids or mono- or polybasic, optionally substituted aliphatic and aromatic phosphonic acids.

Preferred organic acids mentioned are hydroxycarboxylic acids, such as, for example, glycolic acid, lactic acid, tartaric acid and citric acid, with lactic acid being particularly preferred.

Protonation of the polymer takes place either during the polymerization, directly after the polymerization or only during the formulation of the cosmetic preparation, during which a physiologically compatible pH is usually established.

Protonation is understood as meaning that at least some of the protonatable groups of the polymer, preferably at least 20, preferably more than 50, particularly preferably more than 70, most preferably more than 90 mol % is protonated, so that an overall cationic charge of the polymer results.

Of suitability for quaternizing the compounds a) are, for example, alkyl halides having 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride, propyl bromide, hexyl bromide, dodecyl bromide, lauryl bromide and benzyl halides, in particular benzyl chloride and benzyl bromide. A preferred quaternizing agent is methyl chloride. For quaternizing with long-chain alkyl radicals, the corresponding alkyl bromides, such as hexyl bromide, dodecyl bromide or lauryl bromide, are preferred.

Further suitable quaternizing agents are dialkyl sulfates, in particular dimethyl sulfate or diethyl sulfate.

Quaternization of the basic monomers a) can also be carried out with alkylene oxides, such as ethylene oxide or propylene oxide, in the presence of acids.

Preferred quaternizing agents are methyl chloride, dimethyl sulfate or diethyl sulfate, with methyl chloride being particularly preferred.

Quaternization of the polymers with one of the specified quaternizing agents takes place by generally known methods.

The polymers produced by the method according to the invention are preferably used for modifying the rheology of aqueous compositions preferably in the pH range from 1 to 12, particularly preferably from 2 to 10.

In the range from pH 1 to pH 5, it is advantageous if the quaternizable groups of the polymers are present in quaternized form to less than 20%, preferably to less than 10%, particularly preferably to less than 1%.

In the range from pH 6 to pH 10, it is advantageous if the quaternizable groups of the polymers are present in quaternized form to at least 10%, preferably to at least 20% and at most to 99, preferably to at most 90.

In a preferred embodiment of the invention, the quaternizable groups of the polymers obtainable by the method according to the invention are quaternized in the range from 40 to 80, preferably in the range from 50 to 70 mol %.

Between pH 5 and pH 6, the polymers can, depending on their quantitative and/or qualitative monomer composition, be advantageously present either in partially quaternized form or nonquaternized form.

The person skilled in the art discovers through routine experiments whether the quaternizable groups of a polymer produced according to the invention must be present in quaternized form in a certain pH range advantageously to more than 50 mol %, to 50 mol % or to less than 50 mol % in order to achieve the desired effects such as rheology modification. Through further routine experiments it is also possible to ascertain the degree of quaternization best suited for the desired effect (=quotient of amount of the quaternized groups and sum of the amounts of quaternized groups and nonquaternized quaternizable groups).

In one embodiment of the invention, the polymer comprises only monomers a) and c) in copolymerized form.

Monomer b)

The polymer produced by the method according to the invention comprises 0 to less than 25, preferably 1 to 20 and particularly preferably 5 to 20% by weight, of at least one monoethylenically unsaturated amide-group-containing compound b) different from a) in copolymerized form.

Monomer b) is preferably selected from compounds of the general formula IV

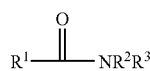

(IV)

where
$R^1$ is a group of the formula $CH_2=CR^4-$ where $R^4=H$ or $C_1$-$C_4$-alkyl and $R^2$ and $R^3$, independently of one another, are H, alkyl, cycloalkyl, heterocycloalkyl, aryl or hetaryl, or $R^2$ and $R^3$, together with the nitrogen atom to which they are bonded, are a five- to eight-membered nitrogen heterocycle or $R^2$ is a group of the formula $CH_2=CR^4-$ and $R^1$ and $R^3$, independently of one another, are H, alkyl, cycloalkyl, heterocycloalkyl, aryl or hetaryl or $R^1$ and $R^3$, together with the amide group to which they are bonded, are a lactam with 5 to 8 ring atoms.

Preferably, the polymer produced by the method according to the invention comprises, as monomer b), at least one N-vinyllactam in copolymerized form. Suitable as N-vinyllactam b) are unsubstituted N-vinyllactams and N-vinyllactam derivatives, which can, for example, have one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. and mixtures thereof.

Preferably, the polymer produced by the method according to the invention comprises monomers b) in incorporated form where, in formula IV, $R^2$ is $CH_2=CH-$ and $R^1$ and $R^3$, together with the amide group to which they are bonded, are a lactam with 5 ring atoms.

As monomers b), particular preference is given to using N-vinylpyrrolidone, N-vinylcaprolactam, N-vinylformamide, (meth)acrylamide or mixtures thereof, with N-vinylpyrrolidone and methacrylamide being most preferred.

In one embodiment, the polymer produced by the method according to the invention comprises merely monomers a) and b) in incorporated form, with N-vinylimidazole being preferred as a) and N-vinylpyrrolidone being preferred as b).

The polymer produced by the method according to the invention comprises less than 25, preferably at most 23 and in particular at most 20% by weight of b) in copolymerized form.

In one embodiment of the invention, the polymer produced by the method according to the invention comprises at least 1, particularly preferably at least 2 and in particular at least 5 and less than 25, preferably at most 20% by weight of b) in copolymerized form.

Crosslinker c)

In a further preferred embodiment of the invention, the crosslinker c) used for producing the polymer suitable for the use according to the invention is selected from compounds with at least 2 ethylenically unsaturated, nonconjugated, radically polymerizable double bonds per molecule.

Suitable crosslinkers c) are, for example, acrylic esters, methacrylic esters, allyl ethers or vinyl ethers of at least dihydric alcohols. The OH groups of the parent alcohols may here be completely or partially etherified or esterified; however, the crosslinkers comprise at least two ethylenically unsaturated groups.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)-cyclohexane, hydroxypivalic neopentyl glycol monoester, 2,2-bis(4-hydroxyphenyl)-propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans with molecular weights of in each case 200 to 10 000.

Apart from the homopolymers of ethylene oxide and propylene oxide, it is also possible to use block copolymers of ethylene oxide or propylene oxide or copolymers which comprise ethylene oxide and propylene oxide groups in incorporated form.

Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. Preferred polyhydric alcohols in this connection are also disaccharides and trisaccharides.

The polyhydric alcohols can of course also be used following reaction with ethylene oxide or propylene oxide as the corresponding ethoxylates and propoxylates. The polyhydric alcohols can also firstly be converted to the corresponding glycidyl ethers by reaction with epichlorohydrin.

Further suitable crosslinkers are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, the monohydric, unsaturated alcohols can also be esterified with polybasic carboxylic acids, for example malonic acid, tartaric acid, trimellitic acid, phthalic acid, terephthalic acid, citric acid or succinic acid. Further suitable crosslinkers are esters of unsaturated carboxylic acids with the above-described polyhydric alcohols, for example oleic acid, crotonic acid, cinnamic acid or 10-undecenoic acid.

Suitable crosslinkers c) are also straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable as crosslinkers are the amides of (meth)acrylic acid, itaconic acid and maleic acid, and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids as have been described above.

Also suitable as crosslinkers are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Also suitable are alkylenebisacrylamides, such as methylenebisacrylamide and N,N'-(2,2)butane and 1,1'-bis(3,3'-vinylbenzimidazolith-2-one)-1,4-butane.

Other suitable crosslinkers are, for example, alkylene glycol di(meth)acrylates, such as ethylene glycol diacrylate, ethylene glycol dimethacrylate, tetraethylene glycol acrylate, tetraethylene glycol dimethacrylate, diethylene glycol acrylate, diethylene glycol methacrylate, vinyl acrylate, allyl acrylate, allyl methacrylate, divinyidioxane, pentaerythritol allyl ether, and mixtures of these crosslinkers.

Further suitable crosslinkers are divinyidioxane, tetraallylsilane or tetravinylsilane.

Particularly preferably used crosslinkers are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Very particularly preferred crosslinkers are pentaerythritol triallyl ether, methylenebisacrylamide, N,N'-divinylethyleneurea, triallylamine and triallylmonoalkylammonium salts, and acrylic esters of ethylene glycol, butanediol, trimethylolpropane or glycerol or acrylic esters of glycol, butanediol, trimethylolpropane or glycerol reacted with ethylene oxide and/or epichlorohydrin. Pentaerythritol triallyl ether is most preferred.

It is of course also possible to use mixtures of the above-mentioned compounds. The crosslinker is preferably soluble in the reaction medium. If the solubility of the crosslinker in the reaction medium is low, then it can be dissolved in a monomer or in a monomer mixture or else be metered in dissolved form in a solvent which is miscible with the reaction medium. Particular preference is given to those crosslinkers which are soluble in the monomer mixture.

The crosslinkers c) are used for the use according to the invention in amounts of at least 0.01, preferably at least 0.02, further preferably at least 0.05 and particularly preferably at least 0.1 and at most 10, preferably at most 5, further preferably at most 2 and particularly preferably at most 1% by weight, based on the total amount of monomers a) to e) used.

In a particularly preferred embodiment of the invention, pentaerythritol triallyl ether is used in an amount of from 0.1% by weight to 0.7% by weight, most preferably in an amount of from 0.3% by weight to 0.6% by weight.

The % amount by weight of crosslinker c) refers to the amount of the mixture of components a) to e) used for producing the polymer.

Further Monoethylenically Unsaturated Compound d)

According to the invention, the monomer mixture to be polymerized also comprises 0 to 15% by weight of at least one monoethylenically unsaturated compound d1) comprising at least one group selected from the group consisting of optionally substituted $C_5$-$C_{30}$-alkyl, $C_5$-$C_{30}$-alkenyl, $C_5$-$C_8$-cycloalkyl, aryl, arylalkyl and hetaryl and/or a reactive precursor (d2) of component d).

Compound d) carries a hydrophobic group in the polymer suitable for the use according to the invention.

The compounds d1) may be monomers which are hydrophobic per se, such as, for example, esters or amides of (meth)acrylic acid with aliphatic $C_5$-$C_{30}$-alcohols or amines, such as, for example, hexyl (meth)acrylate or -(meth)acrylamide, n-heptyl (meth)acrylate or -(meth)acrylamide, n-octyl (meth)acrylate or -(meth)acrylamide, n-nonyl (meth)acrylate or -(meth)acrylamide, n-decyl (meth)acrylate or -(meth)acrylamide, n-undecyl (meth)acrylate or -(meth)acrylamide, n-dodecyl (meth)acrylate or -(meth)acrylamide, n-tridecyl (meth)acrylate or -(meth)acrylamide, n-tetradecyl (meth)acrylate or -(meth)acrylamide, n-pentadecyl (meth)acrylate or -(meth)acrylamide, n-hexadecyl (meth)acrylate or -(meth)acrylamide, n-heptadecyl (meth)acrylate or -(meth)acrylamide, n-octadecyl (meth)acrylate or -(meth)acrylamide and n-nonadecyl (meth)acrylate or -(meth)acrylamide.

The compounds d1) may, for example, also be (meth)acrylic esters of polyalkylene glycols substituted with hydrophobic radicals, such as, for example, alkyl-substituted (meth)acrylic polyethylene glycol esters.

Also suitable as d1) are long-chain allyl ethers or vinyl ethers, such as $C_5$-$C_{30}$-alkyl vinyl ethers or $C_5$-$C_{30}$-alkenyl vinyl ethers.

Also suitable as d1) are radically polymerizable derivatives of polyisobutene comprising olefinically unsaturated groups. Of these, preferred compounds d1) are, for example, reaction products of polyisobutenyl succinic anhydride (PIBSA) with hydroxyalkyl (meth)acrylates and polyisobutenylsuccinimide (PIBSA) with hydroxyalkyl (meth)acrylates.

WO 04/035635, p. 12, l.26 to p. 27, l.2 describes in detail methods of producing polyisobutene derivatives which can then be reacted by customary reactions with components comprising olefinically unsaturated groups to give suitable compounds d). Reference is made to this description here in its entirety. Polyisobutene derivatives which can be reacted to give suitable compounds d) are, for example, the products which are commercially available under the trade names Glissopal® or Kerocom® (each BASF).

In a particularly preferred embodiment of the invention, 2 to 10% by weight of octadecyl vinyl ether and/or behenyl acrylate and/or stearyl methacrylate and/or lauryl (meth)acrylate are used as compounds d).

In a further particularly preferred embodiment of the invention, the compounds d) used are esters of (meth)acrylic acid with polyethylene glycol mono-$C_{16}$-$C_{22}$-alkyl ethers. Preferred polyethylene glycol mono-$C_{16}$-$C_{22}$-alkyl ethers comprise from 25 to 80 units of ethylene oxide per molecule.

For example, compounds d) which can be used are esters of (meth)acrylic acid with Lutensol® AT 25, Lutensol® AT 50 or Lutensol® AT 80.

Also suitable are methacrylic esters of ethoxylated (for example with 25 mol of ethylene oxide) $C_{16}$-$C_{18}$-fatty alcohol mixtures, as are commercially available, for example, as PLEX® O-6877 or PLEX® O-6954 (Degussa).

Within the context of this invention, reactive precursors d2) of component d) are understood as meaning those radically polymerizable monomers which can be covalently linked before or after their incorporation by polymerization by an, if appropriate polymer-analogous, reaction with at least one group selected from the group consisting of optionally substituted $C_5$-$C_{30}$-alkyl, $C_5$-$C_{30}$-alkenyl, $C_5$-$C_8$-cycloalkyl, aryl, arylalkyl and hetaryl. As an example, monoethylenically unsaturated compounds which carry an epoxide group may be mentioned. These epoxide groups can, for example following incorporation by polymerization into a polymer, be covalently linked by reaction with $C_5$-$C_{30}$-alcohols having a $C_5$-$C_{30}$-alkyl chain.

Further preferred compounds d) are selected from the group consisting of $C_{12}$-$C_{30}$-alkyl (meth)acrylates and $C_{12}$-$C_{30}$-alkyl vinyl ethers.

The polymer suitable for the use according to the invention comprises at most 20, preferably at most 15 and particularly preferably at most 10 and preferably at least 1, particularly preferably at least 2 and especially at least 4% by weight of the compound or compounds d) in copolymerized form.

For the use of the polymers as thickeners in skin cosmetic preparations in particular, a fraction of at least 2, preferably at least 4% by weight, of copolymerized component d) is advantageous.

Polyether-Containing Compound f)

The polymer suitable for the use according to the invention is obtainable by polymerization in the presence of from 0 to 70% by weight, based on the amount of components a) to e), of a polyether-containing compound f).

Suitable polyether-containing compounds f) are generally water-soluble or water-dispersible, nonionic polymers which have polyalkylene glycol groups. Preferably, the fraction of polyalkylene glycol groups is at least 40% by weight, based on the total weight of compound f). As polyether-containing compound f), it is possible to use, for example, polyalkylene glycols, polyesters based on polyalkylene glycols, and polyether urethanes.

Component f) is preferably polyethers from the group of polyalkylene oxides based on ethylene oxide, propylene oxide and butylene oxides, polytetrahydrofuran, and polyglycerol. Depending on the type of monomer building blocks used for their preparation, the polyether-containing compounds f) comprise the following structural units:

—$(CH_2)_2$—O—, —$(CH_2)_3$—O—, —$(CH_2)_4$—O—,
—$CH_2$—$CH(CH_3)$—O—, —$CH_2$—$CH(CH_2$—$CH_3)$—O—, —$CH_2$—$CHOR^a$—$CH_2$—O—, in which $R^a$ is $C_1$-$C_{24}$-alkyl, preferably $C_1$-$C_4$-alkyl.

Either homopolymers or copolymers, where the copolymers can comprise the alkylene oxide units in random distribution or in the form of blocks, are suitable.

The compounds f) can additionally have bridging groups, which are selected, for example, from:

—C(=O)—O—, —O—C(=O)—O—, —C(=O)—$NR^b$, —O—C(=O)—$NR^b$, —$NR^c$—(C=O)—$NR^b$— in which $R^b$ and $R^c$, independently of one another, are hydrogen, $C_1$-$C_{30}$-alkyl, preferably $C_1$-$C_4$-alkyl, or cycloalkyl.

Preferably, the polyethers f) have a number-average molecular weight $M_n$ of at least 300.

Preferably, the polyethers f) have the general formula Va or Vb $$R^7\text{---}[(R^8\text{---}O)_u\text{---}(R^9\text{---}O)_v\text{---}(R^{10}\text{---}O)_w\text{---}[A\text{---}(R^8\text{---}O)_u\text{---}(R^9\text{---}O)_v\text{---}(R^{10}\text{---}O)_w]_s\text{---}R^{11}]_n \quad \text{Va}$$

$$\begin{array}{c} R^{11}\text{---}(O\text{---}R^{10})_w\text{---}(O\text{---}R^9)_v\text{---}(O\text{---}R^8)_u \\ \phantom{R^{11}\text{---}(O\text{---}R^{10})_w\text{---}(O\text{---}R^9)_v\text{---}(O\text{---}R^8)_u}\diagdown \\ \phantom{xxxxxxxxxxxxxxxxxxxxxxxxxxxxxxxxxx} N\text{---}R^{12}\text{---}N \\ \phantom{R^{11}\text{---}(O\text{---}R^{10})_w\text{---}(O\text{---}R^9)_v\text{---}(O\text{---}R^8)_u}\diagup \\ R^{11}\text{---}(O\text{---}R^{10})_w\text{---}(O\text{---}R^9)_v\text{---}(O\text{---}R^8)_u \end{array} \begin{array}{c} (R^8\text{---}O)_u\text{---}(R^9\text{---}O)_v\text{---}(R^{10}\text{-}O)_w\text{---}R^{11} \\ \\ \\ (R^8\text{---}O)_u\text{---}(R^9\text{---}O)_v\text{---}(R^{10}\text{-}O)_w\text{---}R^{11} \end{array} \quad \text{Vb}$$

in which:

$R^7$ is hydroxy, amino, $C_1$-$C_{24}$-alkoxy, $R^{13}$—COO—, $R^{13}$—NH—COO— or a polyalcohol radical, $R^8$, $R^9$ and $R^{10}$, independently of one another, are —$(CH_2)_2$—, —$(CH_2)_3$—, —$(CH_2)_4$—, —$CH_2$—CH($CH_3$)—, —$CH_2$—CH($CH_2$—$CH_3$)— or —$CH_2$—$CHOR^{14}$—$CH_2$—, $R^{11}$ is hydrogen, amino-$C_1$-$C_6$-alkyl, $C_1$-$C_{24}$-alkyl, $R^{13}$—C(=O)— or $R^{13}$—NH—C(=O)—, $R^{12}$ is a $C_1$-$C_{20}$-alkylene group whose carbon chain may be interrupted by 1 to 10 nonadjacent oxygen atoms;

$R^{13}$ is $C_1$-$C_{24}$-alkyl, $R^{14}$ is hydrogen, $C_1$-$C_{24}$-alkyl or $R^{13}$—CO—, A is —C(=O)—O—, —C(=O)—B—C(=O)—O— or —C(=O)—NH—B—NH—C(=O)—O—, B is —$(CH_2)_t$—, if desired substituted cycloalkylene, if desired substituted heterocycloalkylene or if desired substituted arylene, n is 1 or, if $R^7$ is a polyalcohol radical, 1 to 8, s is 0 to 500, preferably 0 to 100, t is 1 to 12, preferably 2 to 6, u independently of the others is in each case 1 to 5000, preferably 1 to 1000, v independently of the others is in each case 0 to 5000, preferably 1 to 1000, w independently of the others is in each case 0 to 5000, preferably 1 to 1000.

Preferred components f) are the polyethers of the formula Va.

The terminal primary hydroxyl groups of the polyethers produced on the basis of alkylene oxides, tetrahydrofuran or glycerol, and also the secondary OH groups of polyglycerol may either be free, or else etherified with $C_1$-$C_{24}$-alcohols, esterified with $C_1$-$C_{24}$-carboxylic acids or reacted with isocyanates to give urethanes. Alcohols suitable for this purpose are, for example: primary aliphatic alcohols, such as methanol, ethanol, propanol and butanol, primary aromatic alcohols, such as phenol, isopropylphenol, tert-butylphenol, octylphenol, nonylphenol and naphthol, secondary aliphatic alcohols, such as isopropanol, tertiary aliphatic alcohols, such as tert-butanol and polyhydric alcohols, e.g. diols, such as ethylene glycol, diethylene glycol, propylene glycol, 1,3-propanediol and butanediol, and triols, such as glycerol and trimethylolpropane. The hydroxyl groups can, however, also be exchanged by reductive amination, e.g. with hydrogen/ammonia mixtures under pressure for primary amino groups, or be converted to aminopropylene end groups by cyanoethylation with acrylonitrile and hydrogenation. The capping of the hydroxyl end groups can take place here not only subsequently through reaction with the alcohols or with alkali metal hydroxide solutions, amines and hydroxylamines, but these compounds can be used as Lewis acids, e.g. boron trifluoride, also at the start of the polymerization as initiators. Finally, the hydroxyl groups can also be capped by reaction with alkylating agents, such as dimethyl sulfate.

The alkyl radicals in the formulae Va and Vb may be branched or unbranched $C_1$-$C_{24}$-alkyl radicals, as defined at the beginning, where $C_1$-$C_{12}$-alkyl radicals are preferred and $C_1$-$C_6$-alkyl radicals are particularly preferred.

The average molecular weight $M_n$ of the polyethers is at least 300 and at most 100 000. It is preferably 500 to 50 000, particularly preferably 2000 to 35 000 and very particularly preferably 2000 to 10 000.

Advantageously, polytetrahydrofurans, homopolymers and copolymers of ethylene oxide, propylene oxide, butylene oxide and isobutylene oxide which may be linear or branched are used as graft base b). According to the invention, the term homopolymers is also intended to include those polymers which, apart from the polymerized alkylene oxide unit, also comprise the reactive molecules which have been used for initiating the polymerization of the cyclic ethers or for the terminal capping of the polymer.

Preferred compounds f) are, for example, those polyether-containing compounds which are commercially available under the trade names Pluriol™, Pluronic™, Lutensol™, Pluracol™ and Plurafac™ (each BASF), Lupranol™ (Elastogran) or PolyTHF® (BASF).

In general, polyol macromers can also be used as component f). Such polyol macromers are known to the person skilled in the art. In particular, reference may be made to the polyol macromers disclosed in U.S. Pat. No. 5,093,412 and WO 05/003200, to which reference is hereby made in its entirety.

In a preferred embodiment of the invention, the polymerization is carried out in the presence of polyalkylene-oxide-containing silicones as compounds f).

Suitable polyalkylene-oxide-containing silicones are described, for example, in the following specifications, to the disclosure of which reference is hereby made:

DE patent 16 94 366: It relates to polysiloxane-polyoxyalkylene block copolymers whose polysiloxane block is constructed in a manner known per se and whose polyoxyalkylene block consists of 25 to 70 percent by weight of a polyoxyalkylene with an average molecular weight of from 1600 to 4000 and an ethylene oxide content of from 20 to 100 percent by weight, remainder propylene oxide and, if appropriate, higher alkylene oxides, and 30 to 75 percent by weight of a polyoxyalkylene with an average molecular weight of from 400 to 1200 and an ethylene oxide content of from 65 to 100 percent by weight, remainder propylene oxide and, if appropriate, higher alkylene oxides.

DE-A 25 41 865: The polysiloxane-polyoxyalkylene block copolymers are defined with regard to their polyoxyalkylene blocks such that the one polyoxyalkylene block has an average molecular weight of from 900 to 1300 and consists of 30 to 55% by weight of ethylene oxide, remainder propylene oxide, and the other polyoxyalkylene block has an average molecular weight of from 3800 to 5000 and consists of from 30 to 50% by weight of ethylene oxide, remainder propylene oxide.

EP-A 0 275 563: The described block copolymer comprises three different polyoxyalkylene blocks, namely a block which comprises 20 to 60% by weight of oxyethylene units, with a molecular weight of from 3000 to 5500, a further block with 20 to 60% by weight of oxyethylene units and a molecular weight of from 800 to 2900 and a third block only of polyoxypropylene units and a molecular weight of from 130 to 1200.

Preferred polyalkylene-oxide-containing silicones are described by EP-A 0 670 342. EP-A 0 670 342 describes, on p. 3, l.22 to p. 4, l.56, polysiloxanes with 1) at least two polyether radicals A and B, where the polyoxyalkylene radical A with an average molecular weight of from 600 to 5500 consists of 20 to 100% by weight of oxyethylene units and 80 to 0% by weight of oxypropylene units and the polyoxyalkylene radical B with an average molecular weight of from 700 to 5000 consists of 0 to <20% by weight of oxyethylene units and 100 to 80% by weight of oxypropylene units, and 2) hydrocarbon radicals having 6 to 30 carbon atoms bonded to Si.

Particularly suitable silicone derivatives are the compounds known under the INCI name Dimethicone Copolyols or silicone surfactants, such as, for example, those available under the trade names Abil® (Goldschmidt), Alkasil® (Rhone-Poulenc), Silicone Polyol Copolymer® (Genesee), Belsil® (Wacker), Silwet® (Witco) or Dow Corning® (Dow Corning). These include compounds with the CAS numbers 64365-23-7; 68937-54-2; 68938-54-5; 68937-55-3.

Particularly suitable silicone derivatives are the compounds described in WO 99/04750 p. 10, l.24 to p. 12, l.8 and p. 13, l.3 to l.34.

WO 01/013884 p. 24, l.22 to p. 26, l.41 describes further particularly preferred polyalkylene-oxide-containing silicones.

Reference is made to the abovementioned specifications and citations from the prior art in their entirety.

Particular preference is given to the polymerization of the mixture of the components a) to e) in the presence of, based on the total amount of components a) to e), 5 to 25% by weight of polyethylene glycol with a molecular weight $M_n$ of at least 2000 to at most 35 000, preferably at most 10 000 and/or 5 to 25% by weight of esters of (meth)acrylic acid with polyethylene glycol mono-$C_{16}$-$C_{22}$-alkyl ethers.

The polymerization of the mixture of components a) to e) is preferably carried out in the presence of at most 50, particularly preferably at most 40% by weight of component f), based on the sum of the amounts of components a) to e).

In a further embodiment of the invention, the polymerization of the mixture of components a) to e) is carried out in the presence of from 5 to 70, preferably 10 to 50, particularly preferably 20 to 40% by weight of component f), based on the sum of the amounts of components a) to e).

Further Monomers e)

The polymers suitable for the use according to the invention can, if desired, comprise 0 to 30% by weight of further monoethylenically unsaturated compounds different from a) to d) in copolymerized form.

Preferably, these further monomers e) are selected from esters of α,β-ethylenically unsaturated mono- and dicarboxylic acids with $C_1$-$C_{30}$-alkanols, $C_2$-$C_{30}$-alkanediols and $C_2$-$C_{30}$-amino alcohols, amides of α,β-ethylenically unsaturated mono- and dicarboxylic acids with $C_2$-$C_{30}$-diamines and $C_2$-$C_{30}$-amino alcohols which have one primary or secondary amino group, amides of α,β-ethylenically unsaturated monocarboxylic acids and N-alkyl and N,N-dialkyl derivatives thereof, N-vinylamides of saturated monocarboxylic acids, esters of vinyl alcohol and allyl alcohol with $C_1$-$C_{30}$-monocarboxylic acids, vinyl ethers, α,β-ethylenically unsaturated mono- and dicarboxylic acids, vinyl aromatics, vinyl halides, vinylidene halides, $C_1$-$C_8$-monoolefins, nonaromatic hydrocarbons with at least two conjugated double bonds and mixtures thereof.

Suitable additional monomers e) are methyl (meth)acrylate, methyl ethacrylate, ethyl (meth)acrylate, ethyl ethacrylate, tert-butyl (meth)acrylate, tert-butyl ethacrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate and mixtures thereof.

Suitable additional monomers e) are also the esters of α,β-ethylenically unsaturated mono- and dicarboxylic acids with amino alcohols, preferably $C_2$-$C_{12}$-amino alcohols. These can preferably be $C_1$-$C_8$-monoalkylated or -dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Preference is given to using esters of acrylic acid, esters of methacrylic acid and mixtures thereof.

Also suitable are tert-butylaminoethyl (meth)acrylate, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminocyclohexyl (meth)acrylate etc.

Suitable additional monomers e) are also N-methyl(meth)acrylamide, N-ethyl(meth)acrylamide, N-propyl(meth)acrylamide, N-(n-butyl)(meth)acrylamide, tert-butyl(meth)acrylamide, n-octyl(meth)acrylamide, 1,1,3,3-tetramethylbutyl (meth)-acrylamide, ethylhexyl(meth)acrylamide, n-nonyl (meth)acrylamide, n-decyl(meth)-acrylamide, n-undecyl (meth)acrylamide, tridecyl(meth)acrylamide, myristyl (meth)acrylamide, pentadecyl(meth)acrylamide, palmityl (meth)acrylamide, heptadecyl(meth)acrylamide, nonadecyl (meth)acrylamide, arrachinyl(meth)acrylamide, behenyl (meth)acrylamide, lignocerenyl(meth)acrylamide, cerotinyl (meth)acrylamide, melissinyl(meth)acrylamide, palmitoleinyl(meth)acrylamide, oleyl(meth)acrylamide, linolyl(meth)acrylamide, linolenyl(meth)acrylamide, stearyl (meth)acrylamide, lauryl(meth)acrylamide and mixtures thereof.

Suitable additional monomers e) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc.

Suitable additional monomers e) are also N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacryl-amide.

Suitable additional monomers e) are also acrylamide, methacrylamide, N-vinylformamide, N-vinylacetamide, N-vinylpropionamide and mixtures thereof.

Suitable additional monomers e) are also monoethylenically unsaturated mono- and dicarboxylic acids with 3 to 25, preferably 3 to 6, carbon atoms, which can also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid, fumaric acid, 2-acrylamido-2-methylpropanesulfonic acid, vinylsulfonic acid, vinylsulfuric acid, vinylphosphoric acid, 10-undecenoic acid, 4-pentenoic acid, cinnamic acid, 3-butenoic acid, 5-hexenoic acid, 6-heptenoic acid, 7-octenoic acid, citraconic acid, mesaconic acid, styrenesulfonic acid, styrenesulfuric acid, 3-sulfopropyl acrylate, bis(3-sulfopropyl) itaconate, 3-sulfopropyl methacrylate, 3-allyloxy-2-hydroxypropane-1-sulfonic acid, 2-acrylamido-2-methylethanesulfonic acid, 2-sulfoethyl acrylate, bis (2-sulfoethyl) itaconate, 2-sulfoethyl methacrylate, 3-sulfopropyl methacrylate, 3-allyloxy-2-hydroxypropane-1-sulfonic acid, 3-allyloxy-2-hydroxyethane-1-sulfonic acid, and alkali metal and ammonium salts thereof, in particular sodium and potassium salts thereof.

If anionic and/or anionogenic compounds are used as monomer e), these are copolymerized to at most 10, preferably to at most 5 and particularly preferably to at most 1% by weight, based on the total amount of components a) to e). In a very particularly preferred embodiment of the invention, at most 0.5% by weight of anionic and/or anionogenic compounds are used as monomers e).

Suitable additional monomers e) are also ethylene, propylene, isobutylene, butadiene, styrene, α-methylstyrene, o-chlorostyrene, acrylonitrile, methacrylonitrile, vinyl chloride, vinylidene chloride, vinyl fluoride, vinylidene fluoride, ethers of vinyl alcohol and monoalcohols having 1 to 18 carbon atoms, such as, for example, methyl vinyl ether, esters of vinyl alcohol and monocarboxylic acids having 1 to 18 carbon atoms, such as vinyl acetate, vinyl propionate, vinyl n-butyrate, vinyl laurate and vinyl stearate and mixtures thereof.

Component e) is most preferably selected from the group consisting of methyl methacrylate, butyl acrylate, methacrylamide and mixtures thereof.

Polymerization

According to the invention, the mixture of components a) to e) to be polymerized can, if appropriate in the presence of f), be polymerized either with the help of initiators which form radicals, or else through the action of high-energy radiation, which should also be understood as meaning the action of high-energy electrons.

The method according to the invention is preferably one wherein the water-insoluble initiators A and B are selected such that their respective decomposition temperatures are at least 70° C.

To produce the copolymers according to the invention, at least two radical initiators are used which permit an essentially independent initiation in at least two phases. Here, copolymers with particularly low residual monomer contents are achieved.

Preferably, for the copolymerization, at least two radical initiators are used whose decomposition temperatures are different from one another by at least 10° C. Within the context of the invention, the decomposition temperature is defined as the temperature at which 50% of the molecules decompose into free radicals within 1 hour, i.e. the half-life is 1 hour.

In one embodiment of the invention, the copolymerization takes place for this procedure up until conclusion of the precipitation of the copolymer at a temperature greater than or equal to the lower decomposition temperature and less than the higher decomposition temperature, and following the precipitation a further reaction takes place at a temperature greater than or equal to the higher decomposition temperature.

In one preferred embodiment, the method according to the invention comprises a first polymerization phase at a first polymerization temperature and a second polymerization phase at a second polymerization temperature above the first polymerization temperature, where, for the polymerization, at least two initiators are used whose half-lives at the first polymerization temperature differ in such a way that at least one of these initiators decomposes into radicals during the first polymerization phase and at least one of these initiators does not essentially decompose into radicals during the first polymerization phase and decomposes into radicals during the second polymerization phase. Preferably, in this procedure, the second polymerization phase starts essentially following precipitation of the copolymer. "Essentially" following precipitation of the copolymer is understood as meaning that the copolymer is present in precipitated form preferably to at least 80% by weight, preferably at least 90% by weight, in particular at least 95% by weight, based on the total weight of the copolymer.

The half-life of an initiator can be determined by customary methods known to the person skilled in the art, as described, for example, in the publication "Initiators for high polymers", Akzo Nobel, No. 10737. Preferably, the half-life of the first polymerization initiator at the first polymerization temperature and of the second polymerization initiator at the second polymerization temperature is in a range from about 1 minute to 3 hours, particularly preferably 5 minutes to 2.5 hours. If desired, shorter half-lives, e.g. from 1 second to 1 minute, or half-lives longer than 3 hours can be used, provided it is ensured that the initiator(s) decomposing at the higher temperature decomposes into radicals essentially during the second polymerization phase.

In addition to the first and second polymerization phase, further polymerization phases can be applied at different polymerization temperatures. Thus, it is for example possible to carry out a first polymerization phase at a first polymerization temperature which is selected such that a controlled polymerization (i.e. e.g. while avoiding an undesired temperature increase through the heat of reaction, an excessively high reaction rate, etc.) takes place. Then, e.g. an afterpolymerization can follow at a temperature which is above the first and below the second polymerization temperature and which is selected such that the initiator(s) decomposing at the higher temperature do essentially not decompose into radicals. Following the conclusion of this afterpolymerization, to which, if desired, the initiator decomposing at the lower temperature and/or another initiator decomposing under the conditions of the afterpolymerization can again be added, the second polymerization phase can then follow.

In particular, the method is one in which the decomposition temperatures of initiators A and B differ by at least 10° C., preferably by at least 15, further preferably by at least 20 and in particular by at least 25° C.

Within the scope of the present invention, water-insoluble means that less than 10, preferably less than 1 g, of the initiator, dissolve in 1 liter of water under standard conditions to give a solution which is clear to the human eye.

The water-insoluble initiators A and B are preferably selected from water-insoluble diazo and peroxide compounds.

Initiators A and B suitable for the method according to the invention are selected, for example, from dibenzoyl peroxide, succinyl peroxide, di-tert-butyl peroxide, tert-butyl perbenzoate, tert-butyl perpivalate, tert-butyl peroctoate, tert-butyl peroxy-2-ethylhexanoate, tert-butyl permaleate, benzoyl peroxide, tert-amyl peroxipivalate, cumene hydroperoxide, diisopropyl peroxydicarbamate, bis(o-tolyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, dimethyl 2,2'-azobis(2-methylpropionate) or 2,2'-azobis(2-methylbutyronitrile).

The radical initiators are preferably selected from the group consisting of benzoyl peroxide, tert-amyl peroxypivalate, dimethyl 2,2'-azobis(2-methylpropionate), 2,2'-azobis(2-methylbutyronitrile), 2,2'-azobis(2-methylpropionamide) and tert-butyl peroxy-2-ethylhexanoate.

Suitable initiators are also 2,2'-azobis(4-methoxy-2,4-dimethylvaleronitrile), 2,2'-azobis(2,4-dimethylvaleronitrile), dimethyl 2,2'-azobis(2-methyl propionate), 2,2'-azobis(2-methylbutyronitrile), 1,1'-azobis(cyclohexane-1-carbonitrile), 2,2'-azobis[N-(2-propenyl)-2-methylpropionamide], 1-[(cyano-1-methylethyl)azo]formamide, 2,2'-azobis(N-butyl-2-methylpropionamide), 2,2'-azobis(N-cyclohexyl-2-methylpropionamide). The aforementioned initiators are commercially available, for example, as Wako® and Trigonox® grades.

In one embodiment of the invention, it is preferred to select for the polymerization up to a time at which at least 80, preferably at least 90, particularly preferably at least 95 and in particular at least 99% by weight of monomers a) to e) used have been polymerized, as initiator A, an initiator whose decomposition temperature is lower than that of initiator B by at least 10° C.

The initiator B is preferably used for the so-called afterpolymerization. The afterpolymerization is carried out after at least 80, preferably at least 90, particularly preferably at least 95 and in particular at least 99% by weight of monomers a) to e) used have been polymerized.

The afterpolymerization is preferably carried out at a temperature which is greater than the temperature at which the main polymerization has been carried out.

In one embodiment, the temperature at which the afterpolymerization is carried out is at least 5° C., preferably at least 10° C., particularly preferably at least 15 and in particular at least 20° C. higher than the temperature of the main polymerization.

The amount of the at least one initiator A preferably used for the main polymerization (first reaction phase) is preferably from 0.001 to 2.0, further preferably 0.01 to 1.5, particularly preferably 0.05 to 1.0 and in particular 0.1 to 0.5% by weight, based on the total amount of the monomers a) to e) used.

The amount of the at least one initiator B preferably used for the afterpolymerization (second reaction phase) is preferably from 0.001 to 2.5, further preferably 0.01 to 2.0, particularly preferably 0.1 to 1.5 and in particular 0.3 to 1.0% by weight, based on the total amount of the monomers a) to e) used.

In a preferred embodiment of the invention, the amount by weight of initiator B is greater than the amount of initiator A. It is particularly preferred if the amount by weight of B is at least 1.5 times, further preferably at least 2 times, particularly preferably at least 3 times, the amount by weight of initiator A.

In the case of a preferred initiator combination, the initiator decomposing at the lower temperature is tert-butyl peroxy-2-ethylhexanoate (CAS No. 3006-82-4; Trigonox® 21S) and the initiator decomposing at the higher temperature is selected from tert-butyl peroxypivalate (e.g. Luperox® 11 M75 from Atochem), tert-butyl peroctoate, lauroyl peroxide (LPO, CAS No. 105-74-8) or 2,5-dimethyl-2,5 bis(t-butylperoxy)hexane (Trigonox® 101).

The main polymerization (first reaction phase) takes place in the temperature range from 40 to 200° C., preferably in the range from 50 to 140° C., particularly preferably in the range from 70 to 120° C. It is usually carried out under atmospheric pressure, but can also proceed under reduced or increased pressure, preferably from 1 to 5 bar.

The afterpolymerization (second reaction phase) takes place in the temperature range from 50 to 220° C., preferably in the range from 60 to 150° C., particularly preferably in the range from 80 to 130° C. It is usually carried out under atmospheric pressure, but can also proceed under reduced or increased pressure, preferably from 1 to 5 bar.

The method according to the invention can be carried out semicontinuously by firstly initially introducing some, e.g. about 10%, of the mixture to be polymerized comprising component f), solvent, the monomers a) to e) and initiator A, heating the mixture to polymerization temperature and, following the onset of polymerization, adding the remainder of the mixture to be polymerized according to the progress of the polymerization.

The polymers can also be obtained by initially introducing component f), heating it to polymerization temperature and adding the mixture of monomers a) to e) and initiator A either in one go, batchwise or preferably continuously, and polymerizing.

Suitable solvents for the method according to the invention are, for example, alcohols, such as methanol, ethanol, n-propanol, isopropanol, n-butanol, sec-butanol, tert-butanol, n-hexanol and cyclohexanol and also glycols, such as ethylene glycol, propylene glycol and butylene glycol and also the methyl or ethyl ethers of the dihydric alcohols, diethylene glycol, triethylene glycol, glycerol, dioxane, butyl acetate, ethyl acetate and toluene, with ethyl acetate, butyl acetate and mixtures thereof being particularly preferred.

The polymerization is particularly preferably carried out as precipitation polymerization.

The method according to the invention is preferably a precipitation polymerization. For this polymerization, solvents are used in which the starting materials for the polymerization are soluble and the resulting polymer is insoluble. Suitable solvents are, for example, aromatic hydrocarbons, such as toluene, xylenes, benzene or aliphatic hydrocarbons, such as n-alkanes, cyclohexane, esters of acetic acid, such as ethyl acetate, butyl acetate, ethers, such as, for example, diethyl ether, dipropyl ether, dibutyl ether, methyl tert-butyl ether, diethylene glycol dimethyl ether, ketones, such as acetone, methyl ethyl ketone and mixtures of these solvents. Mixtures of, for example, ethyl acetate and butyl acetate are particularly suitable since in this solvent mixture the polymers are introduced in a form which can be separated off easily (rate of sedimentation is increased) and, moreover, the reaction temperature in mixtures of butyl acetate and ethyl acetate can be selected to be above the boiling temperature of ethyl acetate with simultaneous evaporative cooling by boiling ethyl acetate.

The polymerization is preferably carried out in the presence of less than 69% by weight of cyclohexane and less than 12% by weight of water, based on the total amount of all components present during the polymerization. Preferably, the polymerization is carried out in the presence of less than 50% by weight, particularly preferably less than 40% by weight and in particular in the range from 30 to 0% by weight of cyclohexane. Preferably, the polymerization is carried out in the presence of less than 10% by weight, particularly preferably less than 8% by weight and in particular in the range from 5 to 0% by weight of water.

In a preferred embodiment, the solvent used for the polymerization consists to at least 30, preferably to at least 50 and in particular to at least 70% by weight, of ethyl acetate or n-butyl acetate or mixtures thereof.

In one embodiment of the invention, the solvent consists to 80 to 100, preferably to 90 to 100% by weight, of ethyl acetate and/or n-butyl acetate.

The precipitation polymerization is usually carried out at temperatures of from 20 to 150° C., preferably 40 to 120° C., in particular 60 to 100° C.

The precipitation polymerization is usually carried out at pressures of from 1 to 15 bar, in particular 1 to 6 bar.

The solvent or solvent mixture determines, through the corresponding boiling temperatures, the maximum reaction temperature if the polymerization is carried out under atmospheric pressure. However, polymerizations under pressure are likewise possible.

In general, the precipitation polymerization can be carried out at solids contents up to about 40% by weight. A range between 25 and 40% by weight is preferred. In the case of high solids contents in particular, it is advisable to carry out the polymerization in the presence of a protective colloid polymer. Suitable protective colloid polymers are those which dissolve readily in the solvents used and do not react with the monomers. Polymers suitable as protective colloids are, for example, copolymers of maleic acid with vinyl alkyl ethers and/or olefins having 8 to 20 carbon atoms or corresponding copolymers of maleic acid half-esters with C10-C20-alcohols or else mono- and diamides of maleic acid with C10-C20-alkylamines, and polyvinyl alcohol ethers with alkyl groups which carry 1 to 20 carbon atoms, or else polyvinyl methyl, ethyl, isobutyl or octadecyl ethers. The amount of protective colloid polymer used is normally in the range from 0.05 to 4% by weight (based on monomers), preferably from 0.1 to 2% by weight. It is often advantageous to use mixtures of two or more protective colloid polymers.

The polymerization is carried out by initially introducing solvent, component f), protective colloid polymer and possibly crosslinker c), heating, and carrying out the polymerization by addition of initiator and monomers a), b), d) and e) (possibly dissolved in the same solvent or solvent mixture). However, it is also possible to initially introduce partial amounts of the monomers and of initiator A (e.g. 10%), to heat this mixture to the polymerization temperature and, after the reaction has started, to add the remainder of the mixture to be polymerized according to the progress of the polymerization. It is likewise possible to initially introduce the crosslinker used in partial amounts and to add the remainder together with the residual components. In the case of lower solids contents, it is also conceivable to initially introduce all of the feed materials in a batch reaction.

In a preferred embodiment, the polymerization for producing the polymers suitable for the use according to the invention is carried out in a feed procedure. Here, some or all of the reactants are added completely or in part, batchwise or continuously, together or in separate feeds to a reaction mixture.

Separate feeds are advantageous, for example, if the solubilities of components a) to e) in certain solvents differ significantly. For example, during the copolymerization of vinylimidazole as a) and methacrylamide as b), and the other components c) to e), a method with separate feeds is advantageous since vinylimidazole and methacrylamide vary considerably in their solubilities.

Monomers and initiator are generally metered in over a period from 1 to 10 hours, preferably from 2 to 5 hours.

During the production of the polymers, it is also possible, if appropriate, for other polymers, such as, for example, polyamides, polyurethanes, polyesters, homopolymers and copolymers of ethylenically unsaturated monomers, to be present. Examples of such polymers, also sometimes used in cosmetics, are the polymers known under the trade names Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastma AQ™, Luviset™ grades, Sokalan™ grades, Luviquat™ grades.

Following the afterpolymerization step, the precipitated polymer is isolated from the reaction mixture, for which it is possible to use any general method for isolating the polymers in the conventional precipitation polymerization. Such methods are filtration, centrifugation, evaporation of the solvent or combinations of these methods. For further purification of the polymer from nonpolymerized constituents, the polymer can be washed. For this, the same solvents can in principle be used as are suitable for the polymerization. On account of the advantageous method according to the invention, the amount of residual monomers is very low compared to known methods.

If the polymer is to be dried, it is advisable to undertake solvent exchange after the polymerization or after the alkylation, and to use low-boiling solvents, such as, for example, acetone for the drying.

During the polymerization, it is also possible to use substances with the help of which the molecular weight of the polymers can be controlled and which are usually referred to as regulators.

Regulators

The radical polymerization of the monomer mixture can take place in the presence of at least one regulator. Regulators are preferably used in a use amount of from 0.0005 to 5% by weight, particularly preferably from 0.001 to 2.5% by weight and in particular from 0.01 to 1.5% by weight, based on the total weight of component a) to e).

Regulators (polymerization regulators) is generally the term used for compounds with high chain-transfer constants. Regulators increase the rate of chain-transfer reactions and thus bring about a reduction in the degree of polymerization of the resulting polymers without influencing the gross reaction rate.

With the regulators it is possible to distinguish between monofunctional, bifunctional or polyfunctional regulators, depending on the number of functional groups within the molecule which can lead to one or more chain-transfer reactions. Suitable regulators are described in detail, for example, by K. C. Berger and G. Brandrup in J. Brandrup, E. H. Immergut, Polymer Handbook, 3rd edition, John Wiley & Sons, New York, 1989, p. II/81-II/141.

Suitable regulators are, for example, aldehydes, such as formaldehyde, acetaldehyde, propionaldehyde, n-butyraldehyde, isobutyraldehyde.

In addition, regulators which can also be used are: formic acid, its salts or esters, such as ammonium formate, 2,5-diphenyl-1-hexene, hydroxylammonium sulfate, and hydroxylammonium phosphate.

Further suitable regulators are halogen compounds, e.g. alkyl halides, such as tetrachloromethane, chloroform, bromotrichloromethane, bromoform, allyl bromide, and benzyl compounds, such as benzyl chloride or benzyl bromide.

Further suitable regulators are allyl compounds, such as, for example, allyl alcohol, functionalized allyl ethers, such as allyl ethoxylates, alkyl allyl ethers, or glycerol monoallyl ether.

As regulators, preference is given to using compounds which comprise sulfur in bonded form.

Compounds of this type are, for example, inorganic hydrogensulfites, disulfites and dithionites or organic sulfides, disulfides, polysulfides, sulfoxides and sulfones. These include di-n-butyl sulfide, di-n-octyl sulfide, diphenyl sulfide, thiodiglycol, ethylthioethanol, diisopropyl disulfide, di-n-butyl disulfide, di-n-hexyl disulfide, diacetyl disulfide, diethanol sulfide, di-t-butyl trisulfide, dimethyl sulfoxide, dialkyl sulfide, dialkyl disulfide and/or diaryl sulfide.

Particular preference is given to organic compounds which comprise sulfur in bonded form.

Compounds preferably used as polymerization regulators are thiols (compounds which comprise sulfur in the form of SH groups, also referred to as mercaptans). Preferred regulators are monofunctional, bifunctional and polyfunctional mercaptans, mercaptoalcohols and/or mercaptocarboxylic acids.

Examples of these compounds are allyl thioglycolates, ethyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercaptosuccinic acid, thioglycerol, thioacetic acid, thiourea and alkyl mercaptans, such as n-butyl mercaptan, n-hexyl mercaptan or n-dodecyl mercaptan.

Particularly preferred thiols are cysteine, 2-mercaptoethanol, 1,3-mercaptopropanol, 3-mercaptopropane-1,2-diol, thioglycerol, thiourea.

Examples of bifunctional regulators, which comprise two sulfurs in bonded form, are bifunctional thiols, such as, for example, dimercaptopropanesulfonic acid (sodium salt), dimercaptosuccinic acid, dimercapto-1-propanol, dimercaptoethane, dimercaptopropane, dimercaptobutane, dimercaptopentane, dimercaptohexane, ethylene glycol bisthioglycolates and butanediol bisthioglycolate.

Examples of polyfunctional regulators are compounds which comprise more than two sulfurs in bonded form. Examples thereof are trifunctional and/or tetrafunctional mercaptans.

Preferred trifunctional regulators are trifunctional mercaptans, such as, for example, trimethylolpropane tris(2-mercaptoethanate), trimethylolpropane tris(3-mercapto-propionate), trimethylolpropane tris(4-mercaptobutanate), trimethylolpropane tris(5-mercaptopentanate), trimethylolpropane tris(6-mercaptohexanate), trimethylolpropane tris (2-mercaptoacetate), glyceryl thioglycolate, glyceryl thiopropionate, glyceryl thioethylate, glyceryl thiobutanate, 1,1,1-propanetriyl tris(mercaptoacetate), 1,1,1-propanetriyl tris (mercaptoethanate), 1,1,1-propanetriyl tris (mercaptopropionate), 1,1,1-propanetriyl tris (mercaptobutanate), 2-hydroxmethyl-2-methyl-1,3-propanediol tris(mercaptoacetate), 2-hydroxymethyl-2-methyl-1,3-propanediol tris(mercaptoethanate), 2-hydroxymethyl-2-methyl-1,3-propanediol tris(mercaptopropionate), 2-hydroxymethyl-2-methyl-1,3-propanediol tris (mercaptobutanate).

Particularly preferred trifunctional regulators are glyceryl thioglycolate, trimethylol propane tris(2-mercaptoacetate), 2-hydroxymethyl-2-methyl-1,3-propanediol tris(mercaptoacetate).

Preferred tetrafunctional mercaptans are pentaerythritol tetrakis(2-mercaptoacetate), pentaerythritol tetrakis(2-mercaptoethanate), pentaerythritol tetrakis(3-mercaptopropionate), pentaerythritol tetrakis(4-mercaptobutanate), pentaerythritol tetrakis(5-mercaptopentanate), pentaerythritol tetrakis(6-mercaptohexanate).

Suitable further polyfunctional regulators are Si compounds which form by reacting compounds of the formula (IVa). Also suitable as polyfunctional regulators are Si compounds of the formula

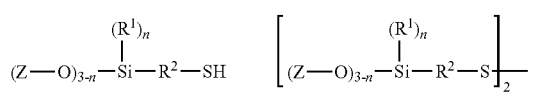

in which
n is a value from 0 to 2,
$R^1$ is a $C_1$-$C_{16}$-alkyl group or phenyl group,
$R^2$ is a $C_1$-$C_{18}$-alkyl group, the cyclohexyl group or phenyl group,
Z is a $C_1$-$C_{18}$-alkyl group, $C_2$-$C_{18}$-alkylene group or $C_2$-$C_{18}$-alkynyl group whose carbon atoms can be replaced by nonadjacent oxygen or halogen atoms, or is one of the groups

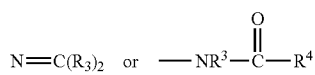

in which
$R_3$ is a $C_1$-$C_{12}$-alkyl group and
$R_4$ is a $C_1$-$C_{18}$-alkyl group.

All of the specified regulators can be used individually or in combination with one another.

In one embodiment of the invention, no regulator is used.

Preference is given to polymers which by polymerization according to the invention of
a) 99.99 to 10% by weight of component a), in particular N-vinylimidazole,
b) 0 to 90% by weight of component b), in particular N-vinylpyrrolidone,
c) 0.01 to 5% by weight of a crosslinker c), in particular pentaerythritol triallyl ether,
d) 0 to 15% by weight of a component d), in particular octadecyl vinyl ether and/or stearyl methacrylate
e) 0 to 30% by weight of a component e), in particular methyl methacrylate, in the presence of
f) 0 to 70% by weight, based on the sum of components a) to e), of a polyether-containing compound f), in particular polyethylene glycol,
wherein
in the course of the method, at least two different water-insoluble initiators A and B are used.

Further preference is given to polymers which are obtainable by radical graft copolymerization of
a) 97.95 to 40% by weight of component a), in particular N-vinylimidazole,
b) 1 to 60% by weight of component b), in particular N-vinylpyrrolidone,
c) 0.05- to 2% by weight of a crosslinker c), in particular pentaerythritol triallyl ether,
d) 1 to 15% by weight of a component d), in particular octadecyl vinyl ether and/or stearyl methacrylate
e) 0 to 20% by weight of a component e), in particular methyl methacrylate, in the presence of
f) 0 to 50% by weight, based on the sum of components a) to e), of a polyether-containing compound f), in particular polyethylene glycol,
wherein
in the course of the method, at least two different water-insoluble initiators A and B are used.

Very particular preference is given to polymers which are obtainable by radical graft copolymerization of
a) 96.9 to 60% by weight of component a), in particular N-vinylimidazole,
b) 1 to 40% by weight of component b), in particular N-vinylpyrrolidone and/or methacrylamide
c) 0.1 to 1% by weight of a crosslinker c), in particular pentaerythritol triallyl ether,
d) 2 to 10% by weight of a component d), in particular octadecyl vinyl ether and/or stearyl methacrylate and/or behenyl acrylate and/or esters of (meth)acrylic acid with polyethylene glycol mono-$C_{16}$-$C_{22}$-alkyl ethers and/or lauryl acrylate,
e) 0 to 10% by weight of a component e), in particular methyl methacrylate, in the presence of
f) 0 to 35% by weight, based on the sum of components a) to e), of a polyether-containing compound f), in particular polyethylene glycol and/or polyethylene glycol mono-$C_{16}$-$C_{22}$-alkyl ether and/or polytetrahydrofuran, with the proviso that the amounts of components a) to e) add up to 100% by weight, wherein in the course of the method, at least two different water-insoluble initiators A and B are used.

Neutralization

Prior to the use as rheology modifier in aqueous and/or alcoholic preparation, the polymer can be neutralized after the polymerization and before or after the filtration. Depending on the choice of monomers a) to e), acids or bases may be required for the neutralization. Neutralizing agents used for monomers carrying basic groups are organic or inorganic acids.

Possible organic acids which may be mentioned are mono- and polybasic, optionally substituted aliphatic and aromatic carboxylic acids, mono- and polybasic, optionally substituted aliphatic and aromatic sulfonic acids or mono- and polybasic, optionally substituted aliphatic and aromatic phosphonic acids, polymers carrying acid groups or ascorbic acid.

Preferred organic acids are hydroxycarboxylic acids, i.e. derivatives of carboxylic acids in which one or more H atoms are replaced by hydroxyl groups.

Examples of hydroxycarboxylic acids which may be mentioned are glycolic acid, lactic acid, tartaric acid and citric acid. Preferred inorganic acids which may be mentioned are phosphoric acid, phosphorous acid, sulfuric acid, sulfurous acid and hydrochloric acid.

Neutralizing agents which may be used for monomers carrying acid groups are, for example, mineral bases, such as sodium carbonate, alkali metal hydroxides, such as NaOH or preferably KOH, and ammonia, organic bases, such as amino alcohols, specifically 2-amino-2-methyl-1-propanol, monoethanolamine, diethanolamine, triethanolamine, triisopropanolamine, tri[(2-hydroxy)-1-propyl]amine, 2-amino-2-methyl-1,3-propanediol, 2-amino-2-hydroxymethyl-1,3-propanediol, and diamines, such as, for example, lysine. In addition, it is also possible to use waterglass as neutralizing agent, as described in DE-A 103 54 015, [0008] to [0010]. It is also possible to advantageously use the amines described in WO 03/99253, p. 2, line 5 to p. 3, line 6 as neutralizing agents.

Modifying the Rheological Properties

Modifying the rheological properties is quite generally understood as meaning the change in deformation behavior and flow behavior of material. The most important rheological properties are viscosity, thixotropy, structural viscosity, rheopexy and dilatancy. These terms are known to the person skilled in the art.

Viscosity is usually understood as meaning the "ropiness" of a liquid. It results from the intermolecular forces in a liquid, is therefore dependent on cohesion (intramolecular) and adhesion (intermolecular). The viscosity characterizes the flow behavior of a liquid. High viscosity means thickness, whereas low viscosity means thinness.

Thixotropy is usually understood as meaning the property of a fluid to exhibit a lower viscosity after shearing and to restore the original viscosity upon standing.

Rheopexy is usually understood as meaning the property of a fluid to exhibit a higher viscosity after shearing. This behavior is closely related to dilatancy, where the viscosity is only higher during shearing.

Within the scope of this invention, modifying the rheology is understood in particular as meaning the increase in viscosity of liquids, usually also referred to as "thickening". This viscosity increase can extend to the formation of gels or solids.

Aqueous, Alcoholic or Aqueous/Alcoholic Compositions

The invention further provides cosmetic, dermatological or pharmaceutical preparations and compositions comprising at least one polymer obtainable by the method according to the invention.

As compositions, preference is given to aqueous, alcoholic or aqueous/alcoholic compositions which comprise the at least one polymer used in an amount in the range from 0.01 to 20, particularly preferably from 0.05 to 10, very particularly preferably from 0.1 to 7% by weight.

Aqueous compositions are understood as meaning compositions which comprise at least 40, preferably at least 50 and in particular at least 60% by weight of water and at the same time less than 20% by weight of alcohol.

Alcoholic compositions are understood as meaning compositions which comprise at least 40, preferably 50% by weight and in particular at least 60% by weight of one or more alcohols and at the same time less than 20% by weight of water.

Aqueous/alcoholic compositions are understood as meaning compositions which comprise at least 20% by weight of water and at the same time at least 20% by weight of alcohol.

A preferred embodiment of the invention are aqueous/alcoholic compositions with preferably at least 50% by weight of water and preferably at most 40% by weight of alcohol.

The polymers obtainable by the method according to the invention are characterized in that they can be used as thickeners for preparations whose liquid phase essentially comprises compounds comprising OH groups. These compounds comprising OH groups are essentially water and alcohols.

The polymers obtainable by the method according to the invention are suitable for modifying the rheology of alcoholic preparations. Suitable alcohols for these preparations are generally all alcohols which are liquid at STP. These are, for example, methanol, ethanol, n-propanol, isopropanol, n-butanol, sec-butanol, tert-butanol, 3-methyl-1-butanol (isoamyl alcohol), n-hexanol, cyclohexanol or glycols, such as ethylene glycol, propylene glycol and butylene glycol, polyhydric alcohols, such as glycerol, diethylene glycol, triethylene glycol, polyalkylene glycols, such as polyethylene glycol, alkyl ethers of these polyhydric alcohols with number-average molecular weights up to about 3000.

Preference is given to cosmetically acceptable alcohols, in particular the alcohol is or comprises ethanol and/or isopropanol, in particular ethanol.

The polymers obtainable by the method according to the invention can act as thickeners and simultaneously as conditioners and setting agents both in alcoholic and essentially anhydrous, aqueous and essentially alcohol-free and aqueous/alcoholic preparations.

The viscosity of the preparations according to the invention is preferably at least 1000, particularly preferably at least 5000 and in particular at least 10 000 and preferably at most 100 000, particularly preferably at most 50 000 and in particular at most 30 000 mPa*s, measured as dynamic viscosity measurement using a Brookfield DV-II+Pro viscometer, spindle 6, 20 revolutions per minute (rpm) at 25° C. depending on the concentration of the polymers, which is selected from the range from 0.2 to 5.0% by weight.

One embodiment of the invention are cosmetic preparations, in particular hair gels on an aqueous, essentially alcohol-free basis with a content of a combination of the polymers obtainable by the method according to the invention and, if appropriate, further ingredients, such as, for example, at least one film-forming and hair-setting polymer.

A further embodiment of the invention are cosmetic preparations, in particular hair gels on an alcoholic, essentially anhydrous basis with a content of a combination of the polymers obtainable by the method according to the invention, at least 30% by weight of $C_1$-$C_4$-alcohols and, if appropriate, an alcohol-soluble, film-forming and hair-setting polymer.

(Hair) gels based on $C_1$-$C_4$-alcohols can satisfy other/complementary requirements for hair gels compared to aqueous or aqueous/alcoholic gels. If, for example, a setting gel is to be prepared, then alcohol-soluble setting polymers can thus also be used.

The polymers obtainable by the method according to the invention are used preferably in an amount of from 0.01 to 20% by weight, particularly preferably from 0.05 to 10% by weight, very particularly preferably from 0.1 to 7% by weight based on the composition. If a hair-setting polymer is used, then it is preferably in an amount of from 0.1 to 20% by weight, particularly preferably from 0.5 to 15% by weight, very particularly preferably from 1 to 10% by weight. The alcohol is preferably used in an amount of from 50 to 99% by weight, particularly preferably from 70 to 98% by weight. The % by weight are in each case based on the total weight of the preparation.

In this case, alcohol-soluble polymers are understood as meaning those polymers which, at 25° C., are soluble to at least 5% by weight in at least one alcohol having 1 to 4 carbon atoms. Liquid alcohols suitable for the hair gels on an alcoholic, essentially anhydrous basis are monohydric or polyhydric alcohols which are liquid at room temperature (20° C.) and have 1 to 4 carbon atoms. These are, in particular, the lower alcohols customarily suitable for cosmetic purposes, such as, for example, ethanol, isopropanol, glycerol, ethylene glycol or propylene glycol. Particular preference is given to monohydric alcohols having 2 to 4 carbon atoms, in particular ethanol and isopropanol. The hair gel is preferably essentially anhydrous, although small amounts of water may be present to improve the solubility of the other ingredients, in which case, however, the alcohol content considerably exceeds the water content. Essentially anhydrous means that the water content is not greater than 10% by weight, preferably not greater than 5% by weight. The alcoholic gels according to the invention are characterized, in the presence of a setting polymer, by good conditioning properties, high degree of setting, rapid drying and pleasant cooling effect.

The preparations according to the invention can be applied to wet or dry hair. The products are suitable both for smooth, wavy and curly hair.

The polymers described above are exceptionally suitable for producing further cosmetic and pharmaceutical compositions. They serve here, for example, as polymeric film formers in preparations for body care, which includes the application of cosmetic preparations to keratinous surfaces, such as skin, hair, nails, and also oral care preparations. They can be used and formulated universally into a very wide range of cosmetic preparations and are compatible with the customary components. In the cosmetic preparations, the polymers suitable for the uses according to the invention can develop particular effects. The polymers can, inter alia, contribute to the moisturization and conditioning of the skin and to the improvement in the feel of the skin.

In the formulations, the polymers act in particular both as thickeners and as conditioners. In particular, the polymers are able, as the sole ingredient of an aqueous composition besides water, in a concentration of 0.5% by weight, to bring about an increase in the viscosity of this composition to at least 10 000 mPa*s (Brookfield viscosity) and an increase in the wet combability of the hair compared to hair treated with just water by at least 10%.

A particular advantage of the invention is that it is possible, with sole use of the abovementioned polymers in aqueous, alcoholic or aqueous/alcoholic compositions, to provide a hair gel suitable as conditioner (conditioner gel). The thickening effect required for hair gels and the conditioning effect required for conditioners can thus be provided by a single ingredient.

Besides the polymers suitable for the uses according to the invention, the compositions according to the invention preferably have at least one cosmetically or pharmaceutically acceptable carrier B) which is selected from
i) water,
ii) water-miscible organic solvents, preferably $C_1$-$C_4$-alkanols,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
vi) fatty acids,
vii) fatty alcohols and
viii) mixtures thereof.

The compositions have, for example, an oil or fat component B) which is selected from: hydrocarbons of low polarity, such as mineral oils; linear saturated hydrocarbons, preferably having more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil and fat components B) are selected from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, pig grease, spermaceti, spermaceti oil, sperm oil, wheat germ oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti, and mixtures of the abovementioned oil and fat components.

Suitable cosmetically and pharmaceutically compatible oil and fat components B) are described in Karl-Heinz Schrader, Grundlagen und Rezepturen der Kosmetika [Fundamentals and formulations of cosmetics], 2nd edition, Verlag Hüthig, Heidelberg, p. 319-355, to which reference is hereby made.

Suitable hydrophilic carriers B) are selected from water, 1-, 2- or polyhydric alcohols having preferably 1 to 8 carbon atoms, such as ethanol, n-propanol, isopropanol, propylene glycol, glycerol, sorbitol, etc.

The cosmetic compositions are skin cosmetic or hair cosmetic compositions.

Preferably, the compositions are used in the form of a spray, gel, foam, ointment, cream, emulsion, suspension, lotion, milk or paste. If desired, liposomes or microspheres can also be used.

The cosmetic, dermatological or pharmaceutical compositions can additionally comprise cosmetically active, dermatologically active or pharmaceutically active ingredients, and auxiliaries.

Preferably, the compositions comprise at least one polymer suitable for the use according to the invention as defined above, at least one carrier B) as defined above and at least one constituent different therefrom which is selected from cosmetically active ingredients, emulsifiers, surfactants, preservatives, perfume oils, further thickeners, hair polymers, hair and skin conditioners, graft polymers, water-soluble or dispersible silicone-containing polymers, photoprotective agents, bleaches, gel formers, care agents, colorants, tints, tanning agents, dyes, pigments, consistency regulators, moisturizers, refatting agents, collagen, protein hydrolyzates, lipids, antioxidants, antifoams, antistats, emollients and softeners.

Further Thickeners/Gel Formers

In addition to the polymers obtainable by the method according to the invention, the cosmetic, dermatological or pharmaceutical compositions can also comprise further thickeners/gel formers. However, it is preferred to use no further thickeners.

Further thickeners/gel formers are preferably present in an amount such that the total amount of thickeners/gel formers is in the range from 0.01 to 10% by weight, in particular from 0.1 to 5% by weight or from 0.5 to 3% by weight.

The additional polymeric gel formers may be synthetic homopolymers or copolymers, where at least one of the monomers carries at least one acid group, preferably a carboxylic acid group, sulfonic acid group or phosphoric acid group.

However, they may also be natural-based polymers, in particular polysaccharides, where at least one type of saccharide is present which has at least one acid group, e.g. glucuronic acid.

Suitable additional synthetic gel formers are constructed, for example, from at least one type of monomer which is selected from acrylic acid, methacrylic acid, itaconic monoesters, acrylamidoalkylsulfonic acids and/or methacrylamidoalkylsulfonic acids.

Synthetic gel formers may, for example, be: crosslinked or uncrosslinked homopolymers of acrylic acid (carbomers) with a molecular weight of, for example, from 2 000 000 to 6 000 000 (corresponding gel formers are commercially available under the trade name Carbopol®), copolymers of acrylic acid and acrylamide, e.g. with a molecular weight of from 2 000 000 to 6 000 000, acrylate/steareth-20 methacrylate copolymer, copolymers of acrylic acid or methacrylic acid with acrylic esters or methacrylic esters (acrylate copolymers), acrylates/C10-30 alkylacrylate crosspolymer, acrylate-vinyl alcohol copolymers, polystyrenesulfonic acid and mixtures thereof.

Natural-based gel formers may be natural or modified natural polymers, e.g.: alginic acid, carrageenan, carboxymethylcellulose, carboxymethylhydroxyethylcellulose, carboxymethyldextran, carboxymethylhydroxypropylguar, cellulose sulfate, dextran sulfate, karaya gum, xanthan gum and mixtures thereof.

Suitable gel formers are, in particular, homopolymers or copolymers formed from at least one ethylenically unsaturated monomer of the general formula (I) $CH_2=CR^1R^2$, where $R^1$ is selected from $A-(CH_2CH_2O)-R^3$ and COOH, A is selected from $C(=O)O$, $C(=O)NH$ and $CH_2O$, x is a number from 1 to 100, preferably from 10 to 50, $R^3$ is a $C_1$- to $C_{30}$-alkyl radical, preferably a $C_8$- to $C_{30}$-alkyl radical, $R^2$ is selected from H, $C_1$-$C_{30}$-alkyl and $CH_2$—$R^1$, with the proviso that at least one of the radicals $R^1$ and $R^2$ comprises the group $A-(CH_2CH_2O)-R^3$. Suitable copolymers are formed, for example, from at least one ethylenically unsaturated monomer of the general formula (I), and at least one ethylenically unsaturated monomer of the general formula (11) $CH_2=C(R^4)COOR^5$ where $R^4$ and $R^5$, independently of one another, are selected from H and an alkyl group having 1 to 30, preferably having 1 to 12, particularly preferably having 1 to 4, carbon atoms. It is preferred that A is selected from $C(=O)O$ and $CH_2O$, that $R^2$ is selected from H and methyl or that the monomer of the formula (I) is an itaconic acid derivative. It is likewise preferred that the monomer of the formula (11) is acrylic acid, methacrylic acid or one of their C1- to C4-alkyl esters. Suitable copolymers are, for example, acrylic or methacrylic acid/acrylic or methacrylic acid polyethoxyalkyl ester copolymers (INCI names: Acrylates/Steareth-20 Methacrylate Copolymer, Acrylates/Palmeth-25 Acrylate Copolymer), as are sold, for example, under the names Acrysol®-22, Acrysol® ICS, Aculyn®-22 or Synthalen® W-2000, or acrylic or methacrylic acid/polyethoxy allyl ether copolymers (INCI name: Steareth-10 Allyl EtherAcrylates Copolymer), as are sold, for example, under the name Salcare® SC 90.

Suitable gel formers are, for example, copolymers constructed from itaconic monoesters of the general formula $CH_2=C(COOR^1)CH_2COOR^2$, where one of the substituents $R^1$ and $R^2$ is hydrogen and the other is the group —$(CH_2CH_2O)-R^3$; x is a number between 1 and 100, preferably between 10 and 40, particularly preferably 20; $R^3$ is an alkyl group having 8 to 30, preferably 12 to 20, carbon atoms, particularly preferably cetyl or stearyl, and at least one second type of monomer selected from acrylate monomers. The acrylate monomers are preferably selected from acrylic acid, methacrylic acid and monoesters thereof, in particular the acrylic alkyl esters and methacrylic alkyl esters having 1 to 10, preferably 1 to 4, carbon atoms in the alkyl group. Suitable copolymers are, for example, acrylic or methacrylic acid/itaconic acid polyethoxyalkyl ester copolymers (INCI names: Acrylates/Steareth-20 Itaconate Copolymer and Acrylates/Ceteth-20 Itaconate Copolymer, Acrylates/Amino-acrylates/C10-30 Alkyl PEG-20 Itaconate Copolymer), as are sold, for example, under the names Structure® 2001, Structure® 3001 and Structure® Plus.

Suitable gel formers are also homopolymers or copolymers constructed from at least one type of monomer selected from acryl- or methacrylamidoalkylsulfonic acid. The polymer is preferably constructed from monomers of the general formula $H_2C=CH—C(=O)—NH-A-SO_3H$, where A is a divalent $C_2$- to $C_6$-, preferably a $C_3$- or $C_4$-hydrocarbon group, particularly preferably the group —C(CH,), —CH,-. This monomer is preferably copolymerized with at least one nonionic radically copolymerizable monomer, in particular a vinyllactam, particularly preferably vinylpyrrolidone. Such a gel former has, for example, the INCI name Ammonium Acryloyidimethyltaurate/VP Copolymer. A suitable commercial product is Aristoflex® AVC. [0019] In addition, non-polymeric and/or nonionic polymeric thickeners, such as, for example, hydroxyethylcellulose, may be present as cothickeners in the composition according to the invention.

Cosmetically and/or Dermatologically Active Ingredients

Suitable cosmetically and/or dermatologically active ingredients are, for example, coloring active ingredients, skin and hair pigmentation agents, tints, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinizing substances, antioxidative active ingredients or active ingredients which act as radical scavengers, skin moisturizing or humectant substances, refatting active ingredients, antierythematous or antiallergic active ingredients and mixtures thereof.

Artificially skin-tanning active ingredients, which are suitable for tanning the skin without natural or artificial irradiation with UV rays, are, for example, dihydroxyacetone, alloxan and walnut shell extract. Suitable keratin-hardening substances are generally active ingredients, as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and as a deodorizing substance which reduces the formation or the intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc.

Suitable photofilter active ingredients are substances which absorb UV rays in the UV-B and/or UV-A region. Suitable UV filters are, for example, 2,4,6-triaryl-1,3,5-triazines in which the aryl groups can in each case carry at least one substituent which is preferably selected from hydroxy, alkoxy, specifically methoxy, alkoxycarbonyl, specifically methoxycarbonyl and ethoxycarbonyl and mixtures thereof. Also suitable are p-aminobenzoic esters, cinnamic esters, benzophenones, camphor derivatives, and pigments which impede UV rays, such as titanium dioxide, talc and zinc oxide.

Photoprotective agents suitable for use in the water-comprising compositions are all of the compounds specified in EP-A 1 084 696 in paragraphs [0036] to [0053], to which reference is hereby made in its entirety.

The list of specified UV photoprotective filters which can be used in the preparations according to the invention is not of course intended to be limiting.

Antimicrobial Agents

In addition, antimicrobial agents can also be used in the water-comprising compositions. In general, these include all suitable preservatives with a specific effect against Gram-positive bacteria, e.g. triclosan (2,4,4'-trichloro-2'-hydroxydiphenyl ether), chlorhexidine (1,1'-hexamethylenebis[5-(4-chlorophenyl)biguanide), and TTC (3,4,4'-trichlorocarbanilide). Commercially available products are Phenonip®, Euxyl® 400, Euxyl® 100 or Euxyl® 500.

Quaternary ammonium compounds are in principle likewise suitable, but are preferably used for disinfectant soaps and washing lotions.

Numerous fragrances also have antimicrobial properties. Specific combinations with particular effectiveness against Gram-positive bacteria are used for the composition of so-called deodorant perfumes.

A large number of essential oils, or characteristic ingredients thereof, such as, for example, oil of cloves (eugenol), mint oil (menthol) or thyme oil (thymol), also exhibit excellent antimicrobial effectiveness.

The antibacterially effective substances are generally used in concentrations of from about 0.1 to 0.3% by weight.

Suitable repellent active ingredients are compounds which are able to deter or repel certain animals, in particular insects, from humans. These include, for example, 2-ethyl-1,3-hexanediol, N,N-diethyl-m-toluamide etc.

Suitable hyperemic substances, which stimulate the flow of blood through the skin, are, for example, essential oils, such as dwarf-pine, lavender, rosemary, juniper berry, horsechestnut extract, birch leaf extract, hayflower extract, ethyl acetate, camphor, menthol, peppermint oil, rosemary extract, eucalyptus oil, etc.

Suitable keratolytic and keratoplastic substances are, for example, salicylic acid, calcium thioglycolate, thioglycolic acid and its salts, sulfur, etc.

Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counteract skin irritations, are, for example, allantoin, bisabolol, dragosantol, chamomile extract, panthenol, etc.

The cosmetic, dermatological or pharmaceutical compositions can comprise at least one further cosmetically or pharmaceutically acceptable polymer as cosmetic and/or pharmaceutical active ingredient (such as also, if appropriate, as auxiliary).

Further Pharmaceutically Active Ingredients

Besides the dermatological active ingredients already specified, active ingredients from the following fields of application can be used: antibiotics, for example sulfonamides, antihistamines, antimycotics, antiphlogistics, antirheumatics, agents for promoting circulation, steroids, such as corticoids, sexual hormones, for example gestagens, wound-healing agents, such as dexpanthenol.

In particular, the following can be used as nonsteroidal, antiinflammatory active ingredients: ibuprofen, ketoprofen, indomethacin, diclofenac, methyl salicylate, hydroxyethyl salicylate, etofenamat.

Further Polymers

Preference is given to compositions which additionally comprise at least one nonionic, anionic, cationic or ampholytic polymer.

Examples of suitable additional anionic polymers are copolymers of acrylic acid and acrylamide and salts thereof; sodium salts of polyhydroxycarboxylic acids, water-soluble or water-dispersible polyesters, polyurethanes and polyureas. Preference is also given to compositions which additionally comprise a polyurethane as anionic polymer.

In a preferred embodiment, the preparations/compositions according to the invention comprise at least one of the customary setting polymers described below.

Particularly suitable additional polymers are the water-soluble or water-dispersible polyurethanes described in DE 4225045 A1, to which reference is hereby made in its entirety. Luviset® P.U.R. (BASF) is particularly suitable.

Particular preference is also given to silicone-containing polyurethanes, as described in DE 19807908 A1, to which reference is hereby made in its entirety. Luviset®Si P.U.R. (BASF) is particularly suitable.

Particularly suitable polymers are copolymers of (meth) acrylic acid and polyether acrylates, where the polyether chain is terminated with a $C_8$-$C_{30}$-alkyl radical. These include, for example, acrylate/beheneth-25 methacrylate copolymers, which are available under the name Aculyn® from Rohm and Haas. Particularly suitable polymers are also copolymers of t-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate, acrylic acid (Ultrahold® 8, strong), copolymers of vinyl acetate, crotonic acid and, if appropriate, further vinyl esters (e.g. Luviset® grades), maleic anhydride copolymers, if appropriate reacted with alcohol, anionic polysiloxanes, e.g. carboxyfunctional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are commercially available, for example, under the names Resyn® (National Starch) and Gafset® (GAF), and vinylpyrrolidone/vinyl acrylate copolymers obtainable, for example, under the trade name Luviflex® (BASF). Further suitable polymers are the vinylpyrrolidone/acrylate terpolymer obtainable under the name Luviflex® VBM-35 (BASF), and sodium sulfonate-containing polyamides or sodium sulfonate-containing polyesters.

In addition, the group of suitable anionic polymers comprises, by way of example, Balance® CR (National Starch; acrylate copolymer), Balance® 0/55 (National Starch; acrylate copolymer), Balance® 47 (National Starch; octylacrylamide/acrylates/butyl-aminoethyl methacrylates copolymer), Aquaflex® FX 64 (ISP; isobutylene/ethyl-maleimide/hydroxyethylmaleimide copolymer), Aquaflex® SF-40 (ISP/National Starch; VP/vinylcaprolactam/DMAPA acrylate copolymer), Allianz® LT-120 (ISP; Rohm & Haas; acrylate/$C_{1-2}$ succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne™ 258 (Rohm & Haas; acrylate/hydroxy ester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX® (National Starch; polyurethane-14 AMP-acrylates copolymer), Resyn® XP (National Starch; acrylates/octylacrylamide copolymer), Fixomer® A-30 (Ondeo Nalco; polymethacrylic acid (and) acrylamidomethylpropanesulfonic acid), Fixate® G-100 (Noveon; AMP-acrylates/allyl methacrylate copolymer).

Suitable additional polymers are also the terpolymers of vinylpyrrolidone, $C_1$-$C_{10}$-alkyl, cycloalkyl and aryl (meth) acrylates and acrylic acid described in U.S. Pat. No. 3,405,084. Suitable additional polymers are also the terpolymers of vinylpyrrolidone, tert-butyl (meth)acrylate and (meth)acrylic acid described in EP-A-0 257 444 and EP-A-0 480 280. Suitable additional polymers are also the copolymers described in DE-A-42 23 066 which comprise at least one (meth)acrylic ester, (meth)acrylic acid, and N-vinylpyrrolidone and/or N-vinylcaprolactam in copolymerized form. Reference is hereby made to the disclosure of these documents.

Suitable carboxylic-acid-group-containing polymers are also carboxylic-acid-group-containing polyurethanes.

EP-A-636361 discloses suitable block copolymers with polysiloxane blocks and polyurethane/polyurea blocks which have carboxylic acid and/or sulfonic acid groups. Suitable silicone-containing polyurethanes are also described in WO 97/25021 and EP-A-751 162. Suitable polyurethanes are also described in DE-A-42 25 045, to which reference is hereby made in its entirety.

These polyurethanes are in principle constructed from
i) at least one compound which comprises two or more active hydrogen atoms per molecule,
ii) at least one diol comprising carboxylic acid groups, or a salt thereof, and
iii) at least one polyisocyanate.

Component i) is, for example, diols, diamines, amino alcohols, and mixtures thereof. The molecular weight of these compounds is preferably in a range from about 56 to 280. If desired, up to 3 mol % of the specified compounds can be replaced by triols or triamines.

Diols i) which can be used are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol. Suitable amino alcohols i) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc. Suitable diamines i) are, for example, ethylenediamine, propylenediamine, 1,4-diaminobutane, 1,5-diaminopentane and 1,6-diaminohexane, and $\alpha,\omega$-diaminopolyethers, which can be prepared by amination of polyalkylene oxides with ammonia.

Component i) may also be a polymer with a number-average molecular weight in the range from about 300 to 5000, preferably about 400 to 4000, in particular 500 to 3000. Polymers i) which can be used are, for example, polyesterdiols, polyetherols and mixtures thereof. Polyetherols are preferably polyalkylene glycols, e.g. polyethylene glycols, polypropylene glycols, polytetrahydrofurans etc., block copolymers of ethylene oxide and propylene oxide or block copolymers of ethylene oxide, propylene oxide and butylene oxide which comprise the copolymerized alkylene oxide units in random distribution or in the form of blocks. Suitable polytetrahydrofurans i) can be prepared by cationic polymerization of tetrahydrofuran in the presence of acidic catalysts, such as, for example, sulfuric acid or fluorosulfuric acid. Such production methods are known to the person skilled in the art. Polyesterdiols i) which can be used preferably have a number-average molecular weight in the range from about 400 to 5000, preferably 500 to 3000, in particular 600 to 2000. Suitable polyesterdiols i) are all those which are usually used for producing polyurethanes, in particular those based on aromatic dicarboxylic acids, such as terephthalic acid, isophthalic acid, phthalic acid, Na or K sulfoisophthalic acid etc., aliphatic dicarboxylic acids, such as adipic acid or succinic acid etc., and cycloaliphatic dicarboxylic acids, such as 1,2-, 1,3- or 1,4-cyclohexanedicarboxylic acid. Suitable diols are, in particular, aliphatic diols, such as ethylene glycol, propylene glycol, 1,6-hexanediol, neopentyl glycol, diethylene glycol, polyethylene glycols, polypropylene glycols, 1,4-dimethylolcyclohexane, etc.

Suitable compounds ii) which have two active hydrogen atoms and at least one carboxylic acid group per molecule are, for example, dimethylolpropanoic acid and mixtures which comprise dimethylolpropanoic acid.

Component iii) is a customary aliphatic, cycloaliphatic and/or aromatic polyisocyanate, such as tetramethylene diisocyanate, hexamethylene diisocyanate, methylenediphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof, in particular isophorone diisocyanate and/or dicyclohexylmethane diisocyanate. If desired, up to 3 mol % of the specified compounds can be replaced by triisocyanates.

Suitable additional polymers are also cationic polymers. These include, for example, polymers with the INCI name Polyquaternium, e.g. copolymers of vinylpyrrolidone/N-vinylimidazolium salts (Luviquat™ FC, Luviquat™ HM, Luviquat™ MS, Luviquat™ Care), copolymers of N-vinylpyrrolidone/dimethylaminoethyl methacrylate, quaternized with diethyl sulfate (Luviquat™ PQ 11), copolymers of N-vinylcaprolactam/N-vinylpyrrolidone/N-vinylimidazolium salts (Luviquat™Hold); cationic cellulose derivatives (Polyquaternium-4 and -10), acrylamido copolymers (Polyquaternium-7) and chitosan. Suitable cationic (quaternized) polymers are also Merquat™ (polymer based on dimethyldiallylammonium chloride), Gafquat™ (quaternary polymers which are formed by reacting polyvinylpyrrolidone with quaternary ammonium compounds), Polymer™ JR (hydroxyethylcellulose with cationic groups) and cationic plant-based polymers, e.g. guar polymers, such as the Jaguar™ grades from Rhodia.

Suitable additional polymers are also amphoteric or zwitterionic polymers, such as the octylacrylamide/methyl methacrylate/tert-butylaminoethyl methacrylate/2-hydroxypropyl methacrylate copolymers obtainable under the names Amphomer™ (National Starch), and zwitterionic polymers, as disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are available commercially under the name Amersette™ (AMERCHOL), and copolymers of hydroxyethyl methacrylate, methyl methacrylate, N,N-dimethylaminoethyl methacrylate and acrylic acid (Jordapon™).

Neutral polymers suitable as additional polymers are, for example, polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex™ Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol™ Plus (BASF), or polyvinylpyrrolidone and copolymers thereof, in particular with vinyl esters, such as vinyl acetate, e.g. Luviskol™ VA 37 (BASF); polyamides, e.g. based on itaconic acid and aliphatic diamines, as described, for example, in DE-A-43 33 238.

Suitable polymers are also nonionic, siloxane-containing, water-soluble or -dispersible polymers, e.g. polyethersiloxanes, such as Tegopren™ (Goldschmidt) or Belsil™ (Wacker).

Compositions for Skin Cleansing and Care

By adding the polymers obtainable by the method according to the invention, it is possible to achieve a considerable improvement in skin compatibility in certain formulations.

The polymers obtainable by the method according to the invention can advantageously also be used in skin cleansing compositions.

Skin cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and gels, foam baths, oil baths and scrub preparations, shaving foams, lotions and creams.

The polymers obtainable by the method according to the invention can also be used for modifying the rheology of cosmetic compositions for the care and protection of the skin, nail care compositions or preparations for decorative cosmetics. Such skin cosmetic compositions are, for example, face washes, face masks, deodorants and other cosmetic lotions. Compositions for use in decorative cosmetics include, for example, cover sticks, stage make-up, mascara and eyeshadows, lipsticks, kohl pencils, eyeliners, blushers, powders and eyebrow pencils.

Furthermore, the polymers obtainable by the method according to the invention can be used in nose strips for pore cleansing, in antiacne compositions, repellents, shaving compositions, hair removal compositions, intimate care compositions, foot care compositions, and in baby care.

The skin care compositions are, in particular, W/O or O/W skin creams, day and night creams, eye creams, face creams, antiwrinkle creams, moisturizing creams, bleach creams, vitamin creams, skin lotions, care lotions and moisturizing lotions.

Skin cosmetic and dermatological compositions comprise preferably 0.05 to 20% by weight, preferably 0.1 to 15% by weight, very particularly preferably 0.1 to 10% by weight, of the polymers obtainable by the method according to the invention, based on the total weight of the composition.

Photoprotective agents in particular, for the rheology modification of which the polymers obtainable by the method according to the invention are used, have the property of increasing the residence time of the UV-absorbing ingredients compared to customary auxiliaries such as polyvinylpyrrolidone.

Depending on the field of use, the compositions can be applied in a form suitable for skin care, such as, for example, as cream, foam, gel, stick, mousse, milk, spray (pumpspray or propellant-containing spray) or lotion.

Besides the rheology-modifying and conditioning polymer and suitable carriers, the skin cosmetic preparations can also comprise further active ingredients and auxiliaries customary in skin cosmetics, as described above. These include, preferably, emulsifiers, preservatives, perfume oils, cosmetic active ingredients, such as phytantriol, vitamin A, E and C, retinol, bisabolol, panthenol, photoprotective agents, bleaches, colorants, tints, tanning agents, collagen, protein hydrolyzates, stabilizers, pH regulators, dyes, salts, other thickeners, gel formers, consistency regulators, silicones, humectants, refatting agents and further customary additives.

Preferred oil and fat components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

To establish certain properties, such as, for example, improvement in feel to the touch, spreading behavior, water resistance and/or binding of active ingredients and auxiliaries, such as pigments, the skin cosmetic and dermatological preparations can comprise further conditioning substances based on silicone compounds. Suitable silicone compounds are, for example, polyalkylsiloxanes, polyarylsiloxanes, polyarylalkylsiloxanes, polyether siloxanes or silicone resins.

Production of the Preparations

The cosmetic or pharmaceutical or dermatological preparations are produced by customary methods known to the person skilled in the art.

In a preferred embodiment of the invention, the cosmetic and dermatological preparations are in the form of gels.

In a further preferred embodiment of the invention, the cosmetic and dermatological preparations are in the form of emulsions, in particular water-in-oil (W/O) or oil-in-water (O/W) emulsions.

It is, however, also possible to choose other types of formulation, for example hydrodispersions, oils, oleogels, multiple emulsions, for example in the form of W/O/W or O/W/O emulsions, anhydrous ointments or ointment bases, etc.

The production of emulsions takes place by known methods. Besides at least one polymer obtainable by the method according to the invention, the emulsions usually comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The choice of additives specific to the type of emulsion and the production of suitable emulsions is described, for example, in Schrader, Grundlagen und Rezepturen der Kosmetika [Fundamentals and formulations of cosmetics], Hüthig Buch Verlag, Heidelberg, 2nd edition, 1989, third part, to which reference is hereby expressly made.

A suitable emulsion, e.g. for a skin cream etc., generally comprises an aqueous phase which is emulsified by means of a suitable emulsifier system in an oil or fatty phase.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karité oil, hoplostethus oil; mineral oils whose distillation start-point under atmospheric pressure is at about 250° C. and whose distillation end-point is at 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase can also comprise silicone oils which are soluble in other oils, such as dimethylpolysiloxane, methylphenylpolysiloxane and the silicone glycol copolymer, fatty acids and fatty alcohols.

In addition, waxes can also be used, such as, for example, carnauba wax, candelilla wax, beeswax, microcrystalline wax, ozokerite wax and Ca, Mg and Al oleates, myristates, linoleates and stearates.

In addition, an emulsion may be in the form of an O/W emulsion. Such an emulsion usually comprises an oil phase, emulsifiers which stabilize the oil phase in the water phase, and an aqueous phase, which is usually in thickened form. Suitable emulsifiers are preferably O/W emulsifiers, such as polyglycerol esters, sorbitan esters or partially esterified glycerides.

Washing, Showering and Bathing Preparations

According to a further preferred embodiment, the rheology-modifying polymers obtainable by the method according to the invention are particularly advantageously used in shower gels, shampoo formulations or bathing preparations.

Moreover, such formulations usually comprise anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and thickeners/gel formers, skin conditioners and humectants.

These formulations comprise preferably 2 to 50% by weight, preferably 5 to 40% by weight, particularly preferably 8 to 30% by weight, of surfactants, based on the total weight of the formulation.

In the washing, showering and bathing preparations, all anionic, neutral, amphoteric or cationic surfactants customarily used in body cleansing compositions can be used.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropyl betaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. In addition, alkylamine oxides, mono- or dialkylalkanolamides, fatty acid esters of polyethylene glycols, ethoxylated fatty acid amides, alkyl polyglycosides or sorbitan ether esters are suitable.

Moreover, the washing, showering and bathing preparations can comprise customary cationic surfactants such as, for example, quaternary ammonium compounds, for example cetyltrimethylammonium chloride.

In addition, the shower gel/shampoo formulations can comprise further thickeners, such as, for example, sodium chloride, PEG-55, propylene glycol oleate, PEG-120 methylglucose dioleate and others, and also preservatives, further active ingredients and auxiliaries and water.

Hair Treatment Compositions

A particularly preferred embodiment of the invention are hair treatment compositions, in particular the thickened preparations and hair gels already described above.

Hair treatment compositions according to the invention preferably comprise at least one polymer obtainable by the method according to the invention in an amount in the range from about 0.01 to 20% by weight, particularly preferably from 0.05 to 10% by weight, very particularly preferably from 0.1 to 7% by weight, based on the total weight of the composition.

As already described in detail, the hair treatment compositions according to the invention are preferably in the form of hair gels.

However, they can also be in the form of hair mousses, shampoos, hair sprays, hair foams, end fluids, neutralizers for permanent waves, hair colorants and bleaches or hot-oil treatments.

Depending on the field of use, the hair cosmetic preparations can be applied in the form of a gel, gel spray, (aerosol) spray, (aerosol) foam, cream, lotion or wax. Hair sprays comprise here both aerosol sprays and pump sprays without propellant gas. Hair foams comprise both aerosol foams and pump foams without propellant gas. Hair sprays and hair foams preferably comprise, predominantly or exclusively, water-soluble or water-dispersible components. If the compounds used in the hair sprays and hair foams according to the invention are water-dispersible, they can be used in the form of aqueous microdispersions with particle diameters of usually 1 to 350 nm, preferably 1 to 250 nm. The solids contents of these preparations are usually in a range from about 0.5 to 20% by weight. These microdispersions generally require no emulsifiers or surfactants for their stabilization.

In one embodiment of the invention, the compositions according to the invention comprise a content of volatile organic components (VOC) of at most 80% by weight, particularly preferably at most 55% by weight.

The hair cosmetic preparations/compositions according to the invention comprise, in one embodiment,
   i. 0.05 to 10% by weight of at least one polymer obtainable by the method according to the invention,
   ii. 20 to 99.95% by weight of water and/or alcohol,
   iii. 0 to 50% by weight of at least one propellant gas,
   iv. 0 to 5% by weight of at least one emulsifier,
   v. up to 25% by weight of further constituents.

Further constituents are understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents can also be, for example, preservatives, perfume oils, opacifiers, active ingredients, UV filters, care substances, such as panthenol, collagen, vitamins, protein hydrolyzates, alpha- and beta-hydroxycarboxylic acids, protein hydrolyzates, stabilizers, pH regulators, dyes, dyes, salts, humectants, refatting agents, complexing agents and further customary additives.

All of the abovementioned ingredients suitable for cosmetic compositions can, if appropriate, also be used for the hair cosmetic compositions. These also include all customary and aforementioned styling, setting and conditioner polymers known in cosmetics.

To establish certain properties, the preparations can additionally also comprise further conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds, such as amodimethicones (CTFA).

Emulsifiers which can be used are all emulsifiers customarily used in hair foams. Suitable emulsifiers may be nonionic, cationic or anionic or amphoteric.

Propellants which are particularly suitable for aerosol foams are mixtures of dimethyl ether and, if appropriate halogenated, hydrocarbons, such as propane, butane, pentane or HFC-152 a. The quantitative ratios of the propellants are to be varied here depending on the other solvents and the desired application.

Examples of nonionic emulsifiers (INCI nomenclature) are laureths, e.g. laureth-4; ceteths, e.g. cetheth-1, polyethylene glycol cetyl ether; cetearths, e.g. ceteareth-25, polyglycol fatty acid glycerides, hydroxylated lecithin, lactyl esters of fatty acids, alkyl polyglycosides.

Examples of cationic emulsifiers are cetyidimethyl-2-hydroxyethylammonium dihydrogenphosphate, cetyltrimonium chloride, cetyltrimonium bromide, cocotrimonium methylsulfate, quaternium-1 to x (INCI).

Anionic emulsifiers can, for example, be selected from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

According to the invention, the polymers can also be used as thickeners in shampoos. Preferred shampoo formulations comprise
   i. 0.05 to 10% by weight of at least one polymer suitable for the use according to the invention,
   ii. 25 to 94.95% by weight of water,
   iii. 5 to 50% by weight of surfactants,
   iv. 0 to 5% by weight of a further conditioner,
   v. 0 to 10% by weight of further cosmetic constituents.

Especially polymers which comprise copolymerized methacrylamide as component b) are suitable for the use as thickener for shampoos and other surfactant-containing compositions.

All anionic, neutral, amphoteric or cationic surfactants customarily used in shampoos can be used in the shampoo formulations.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolaminedodecylbenzenesulfonate, for example, are suitable.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, alkyl polyglycosides or sorbitan ether esters.

Furthermore, the shampoo formulations can comprise customary cationic surfactants, such as, for example, quaternary ammonium compounds, for example cetyltrimethylammonium chloride.

In the shampoo formulations, in order to achieve certain effects, further customary conditioners can also be used besides the polymers of this invention which are also suitable on their own as conditioners. These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). In addition, protein hydrolyzates can be used, as can conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and aminofunctional silicone compounds, such as amodimethicones (CTFA). In addition, cationic guar derivatives, such as guar hydroxypropyltrimonium chloride (INCI), can also be used.

A preparation suitable according to the invention for styling gels can, for example, have the following composition:
 i. 0.1 to 10% by weight of at least one polymer suitable for the use according to the invention,
 ii. 80 to 99.9% by weight of water and/or alcohol,
 iii. 0 to 20% by weight of further constituents.

The use of the polymers suitable for the use according to the invention as gel formers is particularly advantageous if specific rheological or other application properties of the gels are to be established. On account of the excellent compatibility of the polymers suitable for the use according to the invention with further cosmetically customary gel formers, these gel formers can also be used in combination.

In one embodiment of the invention, the preparation thickened according to the invention or the cosmetic gel in one phase is formulated with preferably at least 20% by weight, particularly preferably at least 40% by weight and in particular at least 50% by weight, of water and preferably at most 40% by weight of alcohol. Alcohols which may be present are the lower monoalcohols having 1 to 4 carbon atoms which have already been specified above and which are customarily used for cosmetic purposes, e.g. ethanol and isopropanol.

In a preferred embodiment, the gel comprises, in particular for improving the shine of treated hair, polyhydric alcohols, preferably those having 2 to 6 carbon atoms and having 2 to 6 hydroxy groups in an amount of from 0.1 to 15% by weight, preferably from 1 to 10% by weight. Particular preference is given to glycerol, ethylene glycol and propylene glycol, in particular 1,2-propylene glycol and sorbitol. To improve the shine, silicone oils, in particular polydimethylsiloxanes (dimethicones) and aryl-substituted polydimethylsiloxanes (e.g. phenyltrimethicones), can also be used.

Pigments

In a particular embodiment, the gel according to the invention is suitable for simultaneous conditioning and temporary hair coloration and additionally comprises at least one temporary hair-coloring pigment.

Temporary hair coloration is understood as meaning a color change of human hair which persists to the next hair wash and can be removed again by washing the hair with customary shampoos. The pigments are preferably present in an amount of from 0.01 to 25% by weight, particularly preferably in an amount of from 5 to 15% by weight. The pigments are preferably not nanopigments, but micropigments. The preferred particle size is 1 to 200 µm, in particular 3 to 150 µm, particularly preferably 10 to 100 µm.

The pigments are colorants which are virtually insoluble in the application medium and may be inorganic or organic. Inorganic-organic mixed pigments are also possible. Preference is given to inorganic pigments. The advantage of the inorganic pigments is their excellent resistance to light, weather and temperature. The inorganic pigments can be of natural origin, for example produced from chalk, ocher, umber, green earth, burnt sienna or graphite. The pigments may be white pigments, such as, for example, titanium dioxide or zinc oxide, black pigments, such as, for example, iron oxide black, colored pigments, such as, for example, ultramarine or iron oxide red, luster pigments, metal effect pigments, pearlescent pigments, and fluorescent or phosphorescent pigments, where preferably at least one pigment is a colored, nonwhite pigment. Metal oxides, hydroxides and oxide hydrates, mixed phase pigments, sulfur-containing silicates, metal sulfides, complex metal cyanides, metal sulfates, chromates and molybdates, and the metals themselves (bronze pigments) are suitable. In particular titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 7751 0), carmine (cochineal) are suitable.

Particular preference is given to pigments based on mica which are coated with a metal oxide or a metal oxychloride, such as titanium dioxide or bismuth oxychloride, and if appropriate further color-imparting substances, such as iron oxides, iron blue, ultramarine, carmine etc., and where the color can be determined by varying the layer thickness. Such pigments are sold, for example, under the trade name Rona®, Colorona®, Dichrona® and Timiron® (Merck, Germany).

Organic pigments are, for example, the natural pigments sepia, gamboge, bone charcoal, Cassel brown, indigo, chlorophyll and other plant pigments. Synthetic organic pigments are, for example, azo pigments, anthraquinoids, indigoids, dioxazine, quinacridone, phthalocyanine, isoindolinone, perylene and perinone, metal complex, alkali blue and diketopyrrolopyrrole pigments.

The invention further provides aqueous compositions comprising at least one polymer suitable for the uses according to the invention and at least one further polymer, in particular one which comprises N-vinyllactam in copolymerized form.

Preferred copolymerized N-vinyllactams are unsubstituted N-vinyllactams and N-vinyllactam derivatives which can have, for example, one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. and mixtures thereof. The aqueous compositions particularly preferably comprise at least one polymer suitable for the uses according to the invention and polyvinylpyrrolidone. Here, polyvinylpyrrolidones with a K value of at least 30, preferably at least 60, particularly preferably at least 90, are particularly suitable. Such polyvinylpyrrolidones are available commercially, for example, under the trade name Luviskol™ (BASF). Such compositions exhibit, even at overall concentrations of polymers according to the invention and polymer which comprises N-vinyllactam in copolymerized form (in particular polyvinylpyrrolidone), in the range from about 0.5-10% by weight, preferably 1-5% by weight, in particular as gels, very good properties, such as high viscosity and clarity of the aqueous composition, and very good setting in the case of applications on the hair.

Presentation

It is advantageous if the cosmetic compositions according to the invention are stored in appropriate containers such as, for example, a tube, a small pot, a can, a bottle or squeezy bottle, and used from these. Accordingly, tubes, small pots, cans, bottles or squeezy bottles which comprise a composition according to the invention are also in accordance with the invention.

It is advantageous according to the invention if the cosmetic preparation according to the invention are stored in a can, a small pot, a bottle, squeezy bottle, pump spray or aerosol can and used from this. Accordingly, bottles, squeezy bottles, pump spray or aerosol cans which comprise a preparation according to the invention are also in accordance with the invention.

The preparations according to the invention are advantageously used for caring for the hair, in particular the head hair.

The use of a cosmetic preparation according to the invention as hair shampoo and/or hair conditioner, i.e. as composition for conditioning the hair, is likewise in accordance with the invention.

Pharmaceutical Preparations

Preferred polymers for pharmaceutical preparations comprise N-vinyllactams, in particular N-vinylimidazole, which can also be present in quaternized form, where the quaternization takes place in particular with a methyl group.

In addition, the preparations for topical preparations can comprise customary pharmaceutical auxiliaries in customary amounts.

Suitable auxiliaries are, for example, surfactants. Suitable surfactants are, for example, polyalkoxylated sorbitan acid esters, polyalkoxylated castor oils or polyalkoxylated hydrogenated castor oils, for example Cremophor® grades, such as Cremophor RH 40.

The pharmaceutical preparations are usually essentially aqueous systems. In addition, however, the preparations can also comprise organic solvents such as ethanol, isopropanol, propylene glycol, polypropylene glycols or glycerol.

EXAMPLES

The examples below are intended to illustrate the invention in detail without, however, limiting it thereto.

Production of the Polymers by the Method According to the Invention

In a stirred reactor with nitrogen inlet, reflux condenser and metering device, the initial charge was heated to about 100° C. under nitrogen. Then, feed 1 and ⅓ of feed 2 was added over about 2 hours. The remaining ⅔ of feed 2 were then metered in over about 2 hours. The mixture was left to polymerize at about 100° C. for about a further 2 hours. The mixture was then heated to about 120° C. and feed 3 was metered in over the course of about one hour. The mixture was then left to afterreact for about a further 6 hours in order to achieve the lowest possible content of residual monomers. The mixture was cooled to about 60° C. and decompressed.

The required amount of MeCl was added slowly, the mixture was then heated again to about 100° C. and reacted with stirring for about 2 hours. The mixture was then cooled to room temperature and the device was decompressed. The device was then flushed with nitrogen gas for at least 1 hour. The solids content of the mixtures was generally in the range 25-30% by weight.

The product was filtered, washed with ethyl acetate and dried in vacuo at about 100° C., such that in each case a finely divided white powder was obtained.

The table below shows polymers which have been produced by the method according to the invention and which satisfy the requirements placed on them.

Unless noted otherwise, the quantitative data are in grams [g], the quantitative ratios are ratios by weight (w/w).

Examples

Abbreviations used:
SMA: Steraryl methacrylate
MMA: Methyl methacrylate
MAM: Methacrylamide
n-EtAc: Ethyl acetate
MeCl: Methyl chloride
n-BuAc: n-Butyl acetate
PEG: Polyethylene glycol
VI: N-Vinylimidazole
QVI: N-Vinylimidazolium methyl chloride (VI quaternized with methyl chloride)
VP: N-Vinylpyrrolidone
VFA: N-Vinylformamide
V-Cap: N-Vinylcaprolactam
AS: Acrylic acid
PETAE: Pentaerythritol triallyl ether

| Example No. | 1 | 2 | 3 | 4 | 5 | 6 | 7 |
|---|---|---|---|---|---|---|---|
| Initial charge | | | | | | | |
| n-EtAc [g] | 750 | 750 | 750 | 750 | 750 | 750 | 750 |
| Comp. c) PETAE [g] | 3.38 | 3.38 | — | 3.38 | — | — | — |
| Part of feed 2 [g] | 40 | 40 | 40 | 40 | 40 | 40 | 40 |
| Feed 1 | | | | | | | |
| n-EtAc [g] | 750 | 750 | 750 | 750 | 750 | 750 | 750 |
| b) (VP [g]) | 60 | — | 60 | 75 | 75 | 120 | 37.5 |
| a) (VI [g]) | 675 | 735 | 675 | 675 | 675 | 1080 | 675 |
| d) (SMA [g]) | 15 | 15 | 15 | — | — | — | — |

-continued

|  | | | | | | | |
|---|---|---|---|---|---|---|---|
| e) (MMA [g]) | — | — | — | — | — | — | 37.5 |
| c) (PETAE [g]) | — | — | 3.38 | — | 4.5 | 7.29 | 3.38 |
| Feed 2 | | | | | | | |
| n-EtAc [g] | 732 | 732 | 732 | 732 | 732 | 732 | 732 |
| Initiator 1 | 1.35 | 1.35 | 1.35 | 1.35 | 1.35 | 2.16 | 1.35 |
| Feed 3 | | | | | | | |
| n-EtAc [g] | 214 | 214 | 214 | 214 | 214 | 214 | 214 |
| Initiator 2 | 6.30 | 6.30 | 6.30 | 6.30 | 6.30 | 10.08 | 6.30 |
| Feed 4 | | | | | | | |
| n-EtAc | 562.5 | 562.5 | 562.5 | 562.5 | 562.5 | 562.5 | 562.5 |
| MeCl | 287 | 287 | 287 | 287 | 287 | 460 | 287 |
| Visco 1 | 28000 | 22000 | 23000 | 26000 | 22400 | 23100 | 25000 |
| Visco 0.5 | 15010 | 12 900 | 14000 | 15300 | 14200 | 13800 | 14800 |
| Degree of quat. | 61 | 59 | 60 | 62 | 61 | 59 | 62 |

| Example No. | 8 | 9 | 10 | 11 | 12 | 13 |
|---|---|---|---|---|---|---|
| Initial charge | | | | | | |
| n-EtAc [g] | 750 | 750 | 750 | 750 | 750 | 750 |
| Comp. c) PETAE [g] | — | — | — | — | — | 3.38 |
| Part of feed 2 [g] | 40 | 40 | 40 | 40 | 40 | 40 |
| Feed 1 | | | | | | |
| n-EtAc [g] | 750 | 750 | 750 | 750 | 750 | 750 |
| b) (VP [g]) | 45 | 150 | 45 | 52.5 | 45 | 45 |
| a) (VI [g]) | 690 | 585 | 690 | 675 | 690 | 690 |
| d) (SMA [g]) | — | 15 | 15 | — | — | — |
| e) (MMA [g]) | 15 | — | — | 22.5 | 15 | 15 |
| c) (PETAE [g]) | 3.38 | 3.38 | 3.38 | 3.38 | 3.38 | — |
| Feed 2 | | | | | | |
| n-EtAc [g] | 732 | 732 | 732 | 732 | 732 | 732 |
| Initiator 1 | 1.35 | 1.35 | 1.35 | 1.35 | 1.2 | 1.35 |
| Feed 3 | | | | | | |
| n-EtAc [g] | 214 | 214 | 214 | 214 | 214 | 214 |
| Initiator 2 | 6.30 | 6.30 | 6.30 | 6.30 | 6.30 | 6.30 |
| Feed 4 | | | | | | |
| n-EtAc | 562.5 | 562.5 | 562.5 | 562.5 | 562.5 | 562.5 |
| MeCl | 287 | 287 | 287 | 287 | 287 | 287 |
| Visco 1 | 28000 | 23200 | 23500 | 24100 | 25300 | 28200 |
| Visco 0.5 | 14300 | 12600 | 13200 | 13700 | 14700 | 16050 |
| Degree of quat. | 60 | 71 | 63 | 58 | 62 | 61 |

| Example | 14 | 15 | 16 |
|---|---|---|---|
| Initial charge | | | |
| n-EtAc [g] | 750 | 750 | 750 |
| Comp. c) PETAE [g] | 3.38 | 3.38 | — |
| Part of feed 2 [g] | 40 | 40 | 40 |
| Feed 1 | | | |
| n-EtAc [g] | 750 | 750 | 750 |
| Comp. b) VP [g] | 60 | 60 | 90 |
| Comp. a) VI [g] | 675 | 675 | 600 |
| b) (MAM [g]) | — | — | 30 |
| d) (SMA [g]) | 15 | 15 | — |
| e) (MMA [g]) | — | — | 30 |
| c) (PETAE [g]) | — | — | 3.38 |
| Feed 2 | | | |
| n-EtAc [g] | 732 | 732 | 732 |
| Initiator 1 | 1.2 | 1.35 | 1.35 |
| Feed 3 | | | |
| n-EtAc [g] | 214 | 214 | 214 |
| Initiator 2 | 6.30 | 6.30 | 6.30 |

-continued

| | Feed 4 | | |
|---|---|---|---|
| n-EtAc | — | — | 562.5 |
| MeCl | 287 | 287 | 287 |
| Visco 1 | 28200 | 27600 | 25000 |
| Visco 0.5 | 15200 | 15100 | 14500 |
| Degree of quat. | 61 | 59 | 70 |

Initiator 1: tert-butyl peroctoate (Trigonox ®21 S, tert-butyl peroxy-2-ethylhexanoate, CAS No. 3006-82-4)
Initiator 2: 2,5-dimethyl-2,5-di(tert-butylperoxy)hexane (Trigonox ®101, CAS No. 78-63-7)
\*\* Viscosity: the numerical data are in Pa\*s;
\*\* Visco 1: viscosity of a 1% strength by weight aqueous solution of the alkylated polymer
\*\* Visco 0.5: viscosity of a 0.5% strength by weight aqueous solution of the alkylated polymer
The viscosities of the solutions of polymers 1 to 16 were determined using a Brookfield DV-II+ Pro viscometer under customary conditions using spindle 6 at 20 rpm in a customary 250 ml beaker.
After the preferred method according to the invention (polymerization and alkylation directly one after the other), all of the polymers were filtered, washed and dried.

Application-Related Testing

The polymers described above were subjected to the following application-related tests:

Viscosity:

The viscosities of the gels were determined using a Brookfield DV-II+Pro viscometer under customary conditions using spindle 6 at 20 rpm in a customary 250 ml beaker.

Gel Structure:

A flat spatula was used to spread a 1 mm thick film of the gel on a glass plate. The surface nature of the gel film was then assessed according to the following grading scale: 1=completely smooth and homogeneous, 2=virtually smooth and homogeneous, slight surface structure visible, 3=scarred film, significant surface structure visible, 4=gritty, highly structured Clarity:

A 250 ml beaker with a diameter of about 8 cm was filled with gel without bubbles. Against a black background, the clarity was assessed by looking through compared to a reference gel comprising 0.2% by wt. of Carbopol® Ultrez 21 and 3% by wt. of Luviset® Clear.

Setting (Hand Test):

A hair tress (Caucasian human hair, unbleached, diameter 5 mm) was treated with the hair gel and shaped uniformly in a round (amount of gel applied: 1 g). After drying for 24 hours at 20° C. and 65% relative atmospheric humidity, the setting effect of the hair gel was assessed by bending the hair tress between thumb and index and middle fingers.

Ability to be Washed Out:

A hair tress treated with polymer analogously to the determination of the setting was washed in an approximately 37° C. hot Texapon® NSO solution (6 ml of Texapon® NSO (28% by wt.)) in 1 liter of warm water) for about 15 seconds by immersing and squeezing 5 times. The hair tress was then rinsed until clean and treated again in the same manner. The hair tress was then squeezed well on filter paper and left to dry overnight. The dry hair tress was rolled and analyzed visually and sensorily (hand test) for residues.

Hair gels comprising thickeners according to the invention and 3% Luviskol® K90:

| Example | Concentration of polymer Viscosity [mPas]/pH | Clarity | Structure | Ability to be washed out/feel | Setting |
|---|---|---|---|---|---|
| 1 | 0.5% by wt. 21800/7.4 | slightly cloudy | 2 | still good/ very soft | good |
| 2 | 0.5% by wt. 23050/7.1 | almost clear | 2 | still good/ very soft | good |

-continued

| Example | Concentration of polymer Viscosity [mPas]/pH | Clarity | Structure | Ability to be washed out/feel | Setting |
|---|---|---|---|---|---|
| 3 | 0.5% by wt. 18750/7.4 | slightly cloudy | 2 | still good/ very soft | good |
| 4 | 0.5% by wt. 22900/7.3 | almost clear | 2-3 | still good/ very soft | good |
| 5 | 0.5% by wt. 16700/7.2 | almost clear | 2 | still good/ very soft | very good |
| 6 | 0.5% by wt. 23000/7.4 | slightly cloudy | 2 | still good/ very soft | good |
| 7 | 0.5% by wt. 17060/7.4 | clear | 2 | still good/ very soft | good |
| 8 | 0.5% by wt. 18660/7.2 | clear | 2 | still good/ very soft | good |
| 9 | 0.5% by wt. 17620/7.2 | cloudy | 1-2 | still good/ very soft | good |
| 10 | 0.5% by wt. 15100/6.94 | clear, yellowish | 2-3 | still good/ very soft | very good |
| 11 | 0.5% by wt. 13080/7.29 | clear, yellowish | 2-3 | still good | very good |
| 12 | 0.5% by wt. 17900/7.0 | almost clear | 2-3 | still good | good |
| 13 | 0.5% by wt. 18700/7.2 | almost clear | 3 | still good | good |
| 14 | 0.5% by wt. 15120/7.0 | almost clear | 1-2 | still good | very good |
| 15 | 0.5% by wt. 21100/7.4 | almost clear | 2-3 | still good/ very soft | good |
| 16 | 0.5% by wt. 19600/7.2 | almost clear clear | 2-3 | still good/ very soft | still good |

The invention claimed is:

1. A method for producing polymers by radically polymerizing a) 99.99 to 10% by weight of at least one $\alpha,\beta$-ethylenically unsaturated compound with at least one cationogenic and/or cationic group per molecule, b) 0 to less than 25% by weight of at least one monoethylenically unsaturated amide-group-containing compound different from a), c) 0.01 to 5% by weight of a crosslinker, d) 0 to 15% by weight of at least one monoethylenically unsaturated compound d1) comprising at least one group selected from the group consisting of optionally substituted $C_5$-$C_{30}$ alkyl, $C_5$-$C_{30}$ alkenyl, $C_5$-$C_8$ cycloalkyl, aryl, arylalkyl and hetaryl, e) 0 to 30% by weight of further monoethylenically unsaturated compounds different from a) to d), with the proviso that the amounts of components a) to e) add up to 100% by weight, in the presence of
f) 0 to 70% by weight, based on the sum of components a) to e), of a polyether-containing compound,
wherein
in the course of the process at least two different water-insoluble initiators A and B are used.

2. The method according to claim 1, wherein a) is selected from:
ai) esters of α,β-ethylenically unsaturated mono- and dicarboxylic acids with amino alcohols which may be mono- or dialkylated on an amine nitrogen,
aii) amides of α,β-ethylenically unsaturated mono- and dicarboxylic acids with diamines which have at least one primary or secondary amino group,
aiii) N,N-diallylamines,
aiv) vinyl- and allyl-substituted nitrogen heterocycles,
av) vinyl- and allyl-substituted heteroaromatic compounds and
avi) mixtures thereof.

3. The method according to claim 2, wherein a) is a vinylimidazole of the general formula (I), in which $R^1$, $R^2$ and $R^3$ are selected from hydrogen, $C_1$-$C_4$ alkyl and/or phenyl

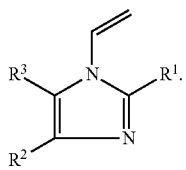
(III)

4. The method according to claim 3, wherein $R^1$ to $R^3$ are hydrogen.

5. The method according to claim 1, wherein at least one component b) is selected from α,β-ethylenically unsaturated amide-group-containing compounds of the general formula IV

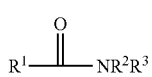
(IV)

wherein
$R^1$ is a group of the formula $CH_2$=$CR^4$— where $R^4$=H or $C_1$-$C_4$ alkyl and $R^2$ and $R^3$, independently of one another, are H, alkyl, cycloalkyl, heterocycloalkyl, aryl or hetaryl, or
$R^2$ and $R^3$, together with the nitrogen atom to which they are bonded, are a five- to eight-membered nitrogen heterocycle or
$R^2$ is a group of the formula $CH_2$=$CR^4$— and $R^1$ and $R^3$, independently of one another, are H, alkyl, cycloalkyl, heterocycloalkyl, aryl or hetaryl or $R^1$ and $R^3$, together with the amide group to which they are bonded, are a lactam with 5 to 8 ring atoms.

6. The method according to claim 4, wherein, in formula IV, $R^2$ is $CH_2$=CH— and $R^1$ and $R^3$, together with the amide group to which they are bonded, are a lactam with 5 ring atoms.

7. The method according to claim 1, wherein the polyether-containing components f) used are compounds of the general formulae Va or Vb

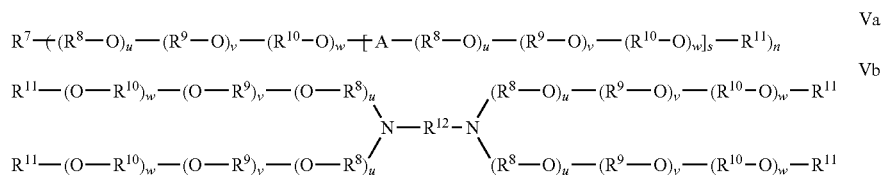

in which:
$R^7$ is hydroxy, amino, $C_1$-$C_{24}$ alkoxy, $R^{13}$—COO—, $R^{13}$—NH—COO— or a polyalcohol radical,
$R^8$, $R^9$ and $R^{10}$, independently of one another, are —(CH_2)_2—, —(CH_2)_3—, —(CH_2)_4—, —CH_2—CH(CH_3)—, —CH_2—CH(CH_2—CH_3)— or —CH_2—CHOR^{14}—CH_2—,
$R^{11}$ is hydrogen, amino-$C_1$-$C_6$ alkyl, $C_1$-$C_{24}$ alkyl, $R^{13}$—C(=O)— or $R^{13}$—NH—C(=O)—,
$R^{12}$ is a $C_1$-$C_{20}$ alkylene group whose carbon chain can be interrupted by 1 to 10 nonadjacent oxygen atoms;
$R^{13}$ is $C_1$-$C_{24}$ alkyl,
$R^{14}$ is hydrogen, $C_1$-$C_{24}$ alkyl or $R^{13}$—CO—,
A is —C(=O)—O—, —C(=O)—B—C(=O)—O— or —C(=O)—NH—B—NH—C(=O)—O—,
B is —(CH_2)_t—, a substituted cycloalkylene, a substituted heterocycloalkylene or a substituted arylene,
n is 1 or, when $R^7$ is a polyalcohol radical, 1 to 8,
s is 0 to 500,
t is 1 to 12,
u is 1 to 5000,
v is 0 to 5000, and
w is 0 to 5000.

8. The method according to claim 6, wherein the polyether-containing component f) is a homopolymer or a copolymer of ethylene oxide and/or propylene oxide with a weight-average molecular weight $M_w$ in the range from 1000 to 100 000, which may be terminally capped at one or both ends.

9. The method according to claim 1, wherein the polyether-containing component f) is present during the polymerization in an amount in the range from 5 to 70% by weight, based on the total amount of components a) to e).

10. The method according to claim 1, wherein the crosslinker c) is selected from the group consisting of: pentaerythritol triallyl ether, methylenebisacrylamide, N,N'-divinylethyleneurea, triallylamine salts, triallylmonoalkylammonium salts, acrylic acid esters of ethylene glycol, acrylic acid esters of butanediol, acrylic acid esters of trimethylolpropane, acrylic acid esters of glycerol, acrylic acid esters of glycol reacted with ethylene oxide and/or epichlorohydrin, acrylic acid esters of butanediol reacted with ethylene oxide and/or epichlorohydrin, acrylic acid esters of trimethylolpropane reacted with ethylene oxide and/or epichlorohydrin, and acrylic acid esters of glycerol reacted with ethylene oxide and/or epichlorohydrin.

11. The method according to claim 1, wherein a mixture to be polymerized comprises 0.05 to 2% by weight of the crosslinker c).

12. The method according to claim 1, wherein compound d) is selected from the group consisting of $C_{12}$-$C_{30}$ alkyl (meth)acrylates and $C_{12}$-$C_{30}$ alkyl vinyl ethers.

13. The method according to claim 1, wherein compound d) is selected from the group consisting of methyl methacrylate, butyl acrylate, methacrylamide and mixtures thereof.

14. The method according to claim 1 wherein the polymer is partially or completely protonated or quaternized in the range from 20 to 99 mol % after or during the polymerization if a non- or only partially protonated or quaternized monomer is used for the polymerization as component a).

15. The method according to claim 1, wherein the initiators A and B are selected such that the respective decomposition temperatures are at least 70° C.

16. The method according to claim 15, wherein the respective decomposition temperatures differ by at least 10° C.

17. The method according to claim 1, wherein quaternization of the polymer is carried out essentially directly after the polymerization in the polymerization solution.

* * * * *